(12) United States Patent
Magro et al.

(10) Patent No.: US 8,340,910 B1
(45) Date of Patent: Dec. 25, 2012

(54) METHOD AND SYSTEM FOR MONITORING SOIL AND WATER RESOURCES

(75) Inventors: Carmen Magro, King of Prussia, PA (US); Jeffrey Campbell, Boise, ID (US)

(73) Assignee: Green Badge LLC, King of Prussia, PA (US)

( * ) Notice: Subject to any disclaimer, the term of this patent is extended or adjusted under 35 U.S.C. 154(b) by 278 days.

(21) Appl. No.: 12/697,226

(22) Filed: Jan. 30, 2010

Related U.S. Application Data

(60) Provisional application No. 61/149,028, filed on Feb. 2, 2009.

(51) Int. Cl.
*G01N 33/24* (2006.01)

(52) U.S. Cl. .......................................................... 702/2

(58) Field of Classification Search ....................... 702/2
See application file for complete search history.

(56) References Cited

OTHER PUBLICATIONS

J.D. Rhoades, Soil salinity assessment, Rome 1999, p. 1-150.*

* cited by examiner

*Primary Examiner* — Tung S Lau
(74) *Attorney, Agent, or Firm* — Clause Eight IPS; Michael Catania

(57) ABSTRACT

A system and method for monitoring soil and water resources is disclosed herein. Sensors capable of monitoring soil temperature, moisture and salinity are utilized with other sensors capable of monitoring such values as air temperature in order to provide real-time parameters to users/operators of land area in order to optimize plant and turf growth, and to optimize water usage.

5 Claims, 36 Drawing Sheets

METHOD AND SYSTEM FOR MONITORING SOIL AND WATER RESOURCES

CROSS REFERENCE TO RELATED APPLICATION

The present application claims priority to U.S. Provisional Patent Application No. 61/149,028, filed on Feb. 2, 2009, which is hereby incorporated by reference in its entirety.

STATEMENT REGARDING FEDERALLY SPONSORED RESEARCH OR DEVELOPMENT

Not Applicable

BACKGROUND OF THE INVENTION

1. Field of the Invention

The present invention relates to monitoring soil conditions. More specifically, the present invention relates to a method and system for monitoring soil and water conditions.

2. Description of the Related Art

The prior art discloses various irrigation systems.

The current method of collecting data in the soil is by way of wired technology or with handheld units. However, due to the impracticality of these units since they either do not contain enough sensors to make a valid representative sample of a site whether it is a field, sports field, golf course, residential or agricultural facility. With regard to the handheld units it is impossible to measure substantial area in real time to make a representative sample.

Prior to the present invention, it would take the use of expensive wired installations and/or handheld sensing equipment to take data from the soil. However, the calculation of this data would not cover large areas representatively since they would be sparse across a full facility or area. In addition these would not be in real time full facility representation. The present invention offers the unique and protocol "look" under the surface with real time calculations and interpretation of what the soil conditions are and more importantly what the manager can do to correct or manage those conditions . . . all in an effort to reduce irresponsible water use, power use, fertilizer use or pesticide use (amongst other things) by knowing exactly what is going on in the soil and what it means for plant health and performance.

BRIEF SUMMARY OF THE INVENTION

The present invention provides a solution to the problems of the prior art.

With the wireless technology of the present invention, it is not only possible to place sufficient sensors in the ground to offer a representative sample of a facility, the sensors are preferably non-disruptive, easy to install and offer real time wireless communication of data. The data is preferably collected through sent to a server to effectively perform the real time calculations. The present invention solves a very huge problem in turfgrass, sports turf, residential/commercial and agricultural soil/plant management environments.

The present invention offers insight as to what is taking place in the soil at any point throughout the day. Since most irrigation models are based on timing and traditional plant needs as found through sampled data in the past, the present invention offers the ability for a manager to make real time decisions based off of real time soil conditions. This offers the ability to water a plant only when it truly needs water based off of the soil conditions. Furthermore, the present invention calculates growing degree days based off of soil conditions rather than ambient conditions. Since many pathogens, insects and stresses such as root and shoot loss are directly related to soil conditions and some of the negative responses from these stresses can occur within minutes of such stress, the present invention offers insight to see the stress before it actually shows symptoms at the surface. This knowledge allows a manager to optimize plant health, yield and performance while virtually eliminating the overuse of water and power.

The variables measured by the sensors of the present invention preferably include real time soil moisture, temperature and salinity. These variables can be measured at any depth so that predictions and indexes can be developed based on individual sites while trends can be drawn up from a database that consists of data from a vast number of facilities worldwide.

The solution to the problem is the unique offering of soil conditions and interpretations of those conditions that would otherwise not be possible over significant areas of a facility. The solutions, suggestions, trends, graphs and calculations from the present invention offer information to the turf manager, facility manager, agricultural manager or any other person in charge of making sound decisions for plant, soil and irrigation practices.

One aspect of the present invention is a method for monitoring real-time conditions of a land area. The method includes monitoring a land area condition from at least one sensor. The method also includes determining at least one parameter from the monitored land area condition. The method also includes displaying the at least one parameter to an operator of the land area.

Another aspect of the present invention is to take real time soil monitoring data and use it to index plant physiological activities as they relate to specific soil conditions. This data can also be used in conjunction with ambient data to make further predictions, models and trend indexes for soil, water and plant activities. The data model can further be used to show real time value of water and power reduction practices while optimizing such use for plant growth and environmental sensitivity. This indexing, modeling and trending will be utilized in a software-based user friendly platform that will show real time calculations based off of AST patented wireless soil sensing information.

Yet another aspect of the present invention is a method for monitoring at least one real-time condition of an upper soil area and a lower soil area of a land area. The method includes monitoring an upper soil condition from a plurality of sensors positioned within an upper soil. The method also includes monitoring a lower soil condition from a plurality of sensors positioned within a lower soil. The method also includes obtaining a real-time parameter from the upper soil and lower soil conditions.

Yet another aspect of the present invention is a system for monitoring real-time conditions of a land area. The system includes a plurality of sensors, means for transmitting to a processor, and means for communicating the at least one parameter. Each of the plurality of sensors is configured to monitor at least one soil condition. The processor is configured to calculate at least one parameter from the monitored soil condition. The communicating means communicates the at least one parameter to an operator of the land area.

The present invention takes the guess work out of trying to manage a plant/soil environment without knowing what is going on in the soil. Having the soil condition data is one thing. Interpreting the data to develop sound decisions is what the present invention specifically does. One example is a golf course manager notices his/her turfgrass declining by way of off-colored turf or reduced growth. By knowing exactly what the soil moisture, temperature and salinity levels are, the present invention eliminates variables that are not the cause of the decline.

For instance, the present invention knows that when the soil temperature reaches a critical level in the upper soil profile the root growth ceases to proliferate. The response in the turf typically takes 72 hours or more to show the effects of that "trigger." The present invention knows exactly when the condition occurs and the manager is able to make decisions . . . offered in the present invention's suggestive solutions . . . that help manage through the soil/plant condition while reducing the risk of turf loss. Another example is effective water management. For instance, every soil has a particular porosity or total pore space. The soil has solids (minerals) and pores. The porosity is the measurement of the pore space portion.

In addition, soil and its particular porosity have a specific field capacity. Field capacity is the point that the soil can no longer hold water against the force of gravity. When the water stops draining out of the rootzone by way of gravity a soil is then said to be at field capacity. Research and experience has shown that plants perform best at approximately 70-75% of field capacity. The present invention determines the porosity and field capacity from lab soil analysis, and makes predictions of these factors based off of water movement and activity as measured with the system sensors.

Knowing what the "target" moisture percentage is . . . for example 22% volumetric water content (VWC), the variable directly measured by a water sensor, the present invention tells where a soil is at any time in relation to this optimal target. Rather than watering based on speculation, the present invention makes irrigation decisions based exactly off of soil conditions. More importantly the present invention helps a manager alter his/her irrigation practices to stay within the target range as defined by the present invention . . . and furthermore the present invention reduces the level of moisture over time to find the optimal range based off of the performance or yield targeted. This further reduces water use. Research has show that predictions of water savings based off of soil monitoring can reach 80% or more. These are just a couple of examples of decisions that are made from real time monitoring by the present invention. Since soil salinity, temperature and moisture affect and are influenced by nearly every practice a manager employs, the value of the present invention for efficient soil/plant/water management is truly endless.

The present invention provides information and interpretation of data that would otherwise not be available to the manager.

Inputs include real time soil data consisting of soil temperature, moisture and salinity at multiple depths. Inputs also include weather variables such as precipitation, wind, temperature, relative humidity, solar radiation and leaf wetness.

Outputs include correlated ambient data with soil data to further define predictive plant reactions based off of that data. Such things as Evapotranspiration (ET) calculation is based off of the scientifically-accepted Penman-Monteith calculation. However, this calculation is based off of ambient conditions. The present invention takes this calculation and alters it based off of specific soil qualities knowing that moisture in the soil can greatly affect this calculation. ET calculations have historically been used to make irrigation decisions. The present invention shows real time soil conditions for making these decisions, but also correlates this data with ET calculations for even more accuracy. Outputs also include calculations of growing degree days, thresholds, trends from this data.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
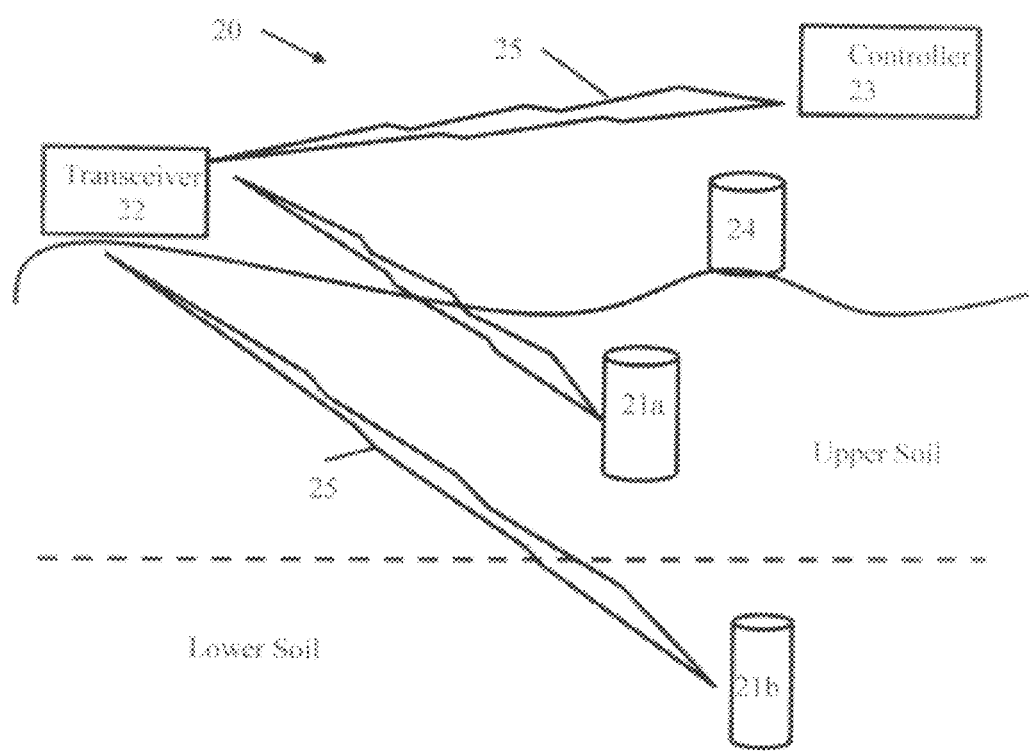
FIG. 1 is a schematic diagram of a preferred embodiment of a system of the present invention.
Figure 1A:
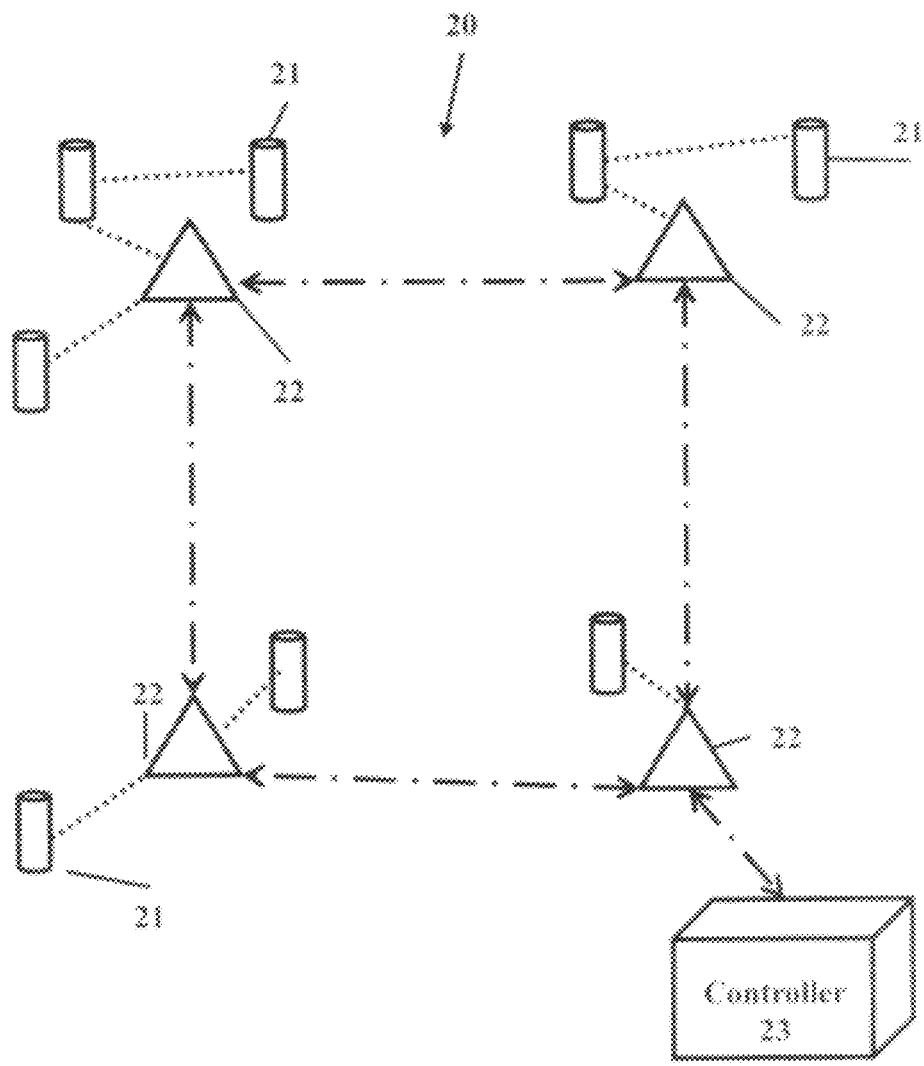
FIG. 1A is a schematic diagram of a preferred embodiment of a system of the present invention illustrating a mesh network established by the transmitters of the system.
Figure 1B:
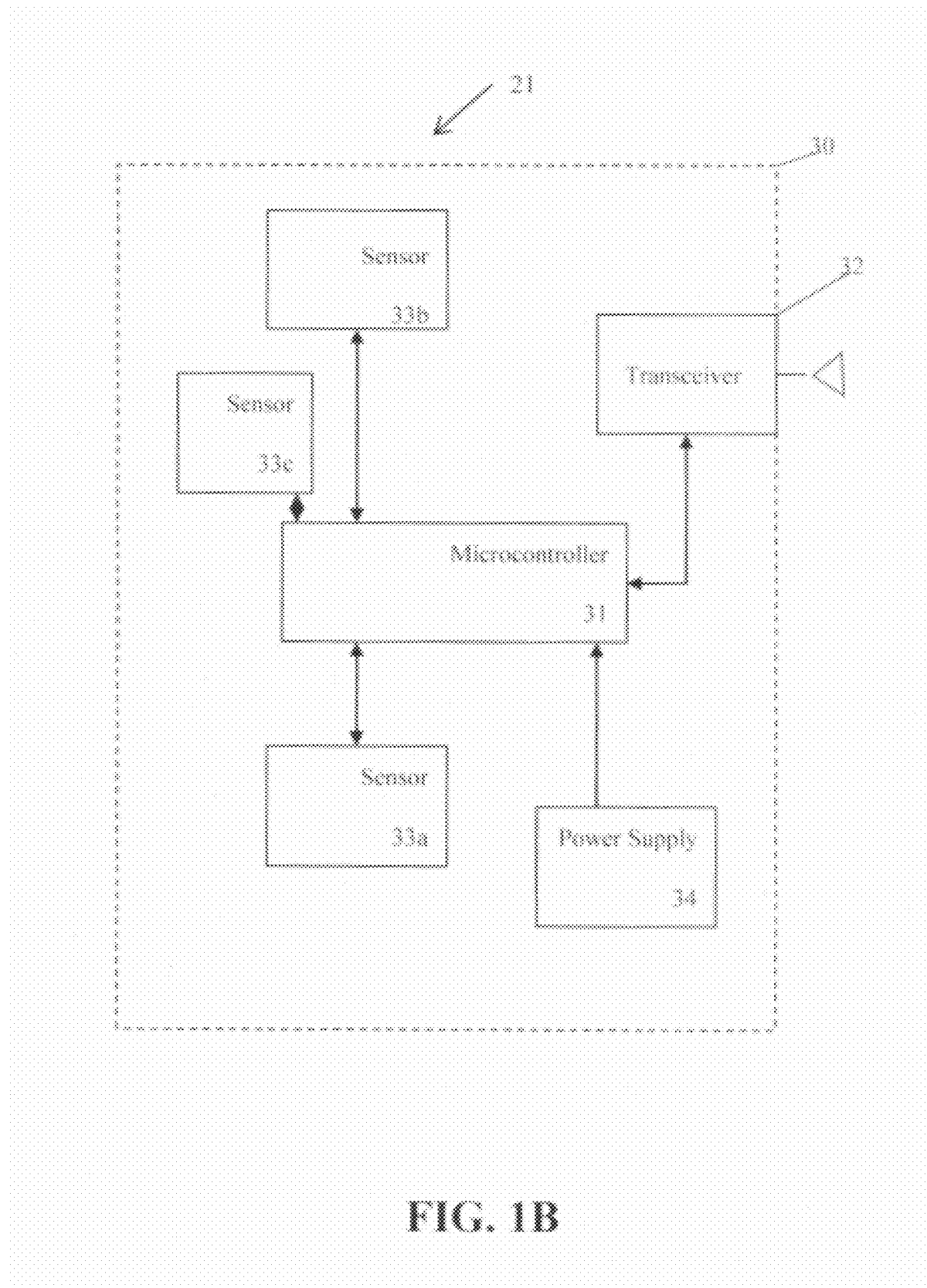
FIG. 1B is a schematic diagram of a preferred embodiment of a sensor node of the system.

As shown in FIGS. 1, 1A and 1B, a preferred embodiment of a system of the present invention is generally designated 20. The system preferably includes a plurality of sensor nodes 21 (upper soil 21a and lower soil 21b), a plurality of above-ground transceivers/transmitters 22, a controller located at an operations center, and a plurality of above-ground sensors 24. The above ground sensors 24 preferably measures air temperature, wind speed, and relative humidity.

Further details of such a system and method are disclosed in Glancy, et al., U.S. Patent Publication Number 2006/0178847 for an Apparatus And Method For Wireless Real Time Measurement And Control Of Soil And Turf Conditions, which is hereby incorporated by reference in its entirety.

FIG. 1B illustrates a sensor node 21 preferably utilized in the system 20. The node 21 preferably has a housing 30, a processor 31, a transceiver 32, sensors 33a, 33b and 33c, and a power supply 34. The sensors are preferably salinity, moisture and temperature sensors 33.

Figure 1C:
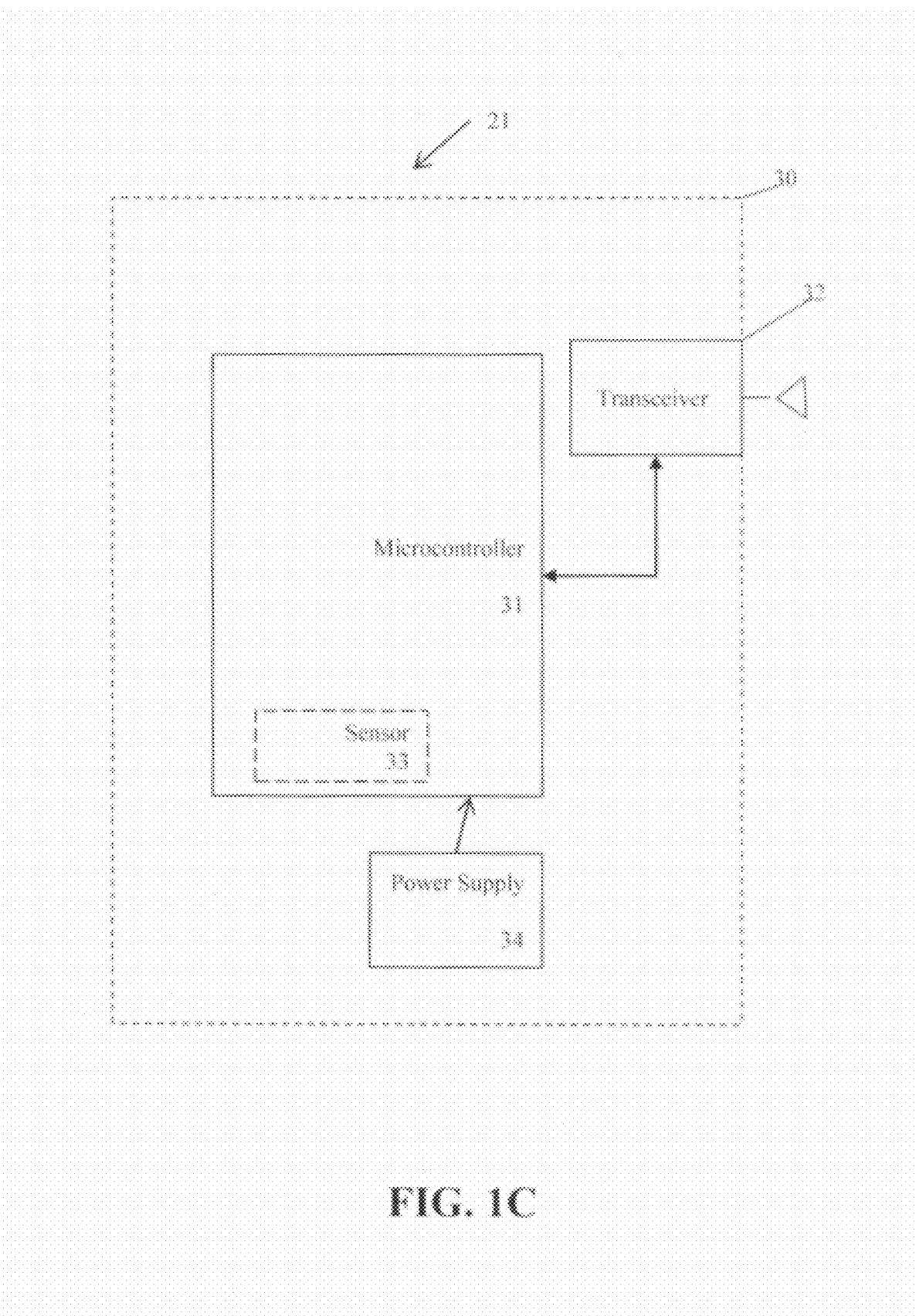
FIG. 1C is a schematic diagram of an alternative embodiment of a sensor node of the system.

FIG. 1C illustrates a sensor node 21 alternatively utilized in the system 20. The node 21 preferably has a housing 30, a processor 31 with an integrated sensor 33, a transceiver 32, and a power supply 34.

Further details of sensors are as disclosed in Campbell, U.S. Pat. No. 7,482,820 for a Sensor For Measuring Moisture And Salinity, which is hereby incorporated by reference in its entirety. An additional sensor and irrigation system is disclosed in Campbell et al., U.S. Provisional Patent Application No. 61/149,330 for a Method And System For Soil And Water Resources, filed on Feb. 2, 2009, which is hereby incorporated by reference in its entirety, and the non-provisional patent application of this provisional patent application, which is Campbell et al., for a Method And System For Soil And Water Resources, U.S. patent application Ser. No. 12/697,254, filed on a date herewith, and hereby incorporated by reference in its entirety.

Figure 2:
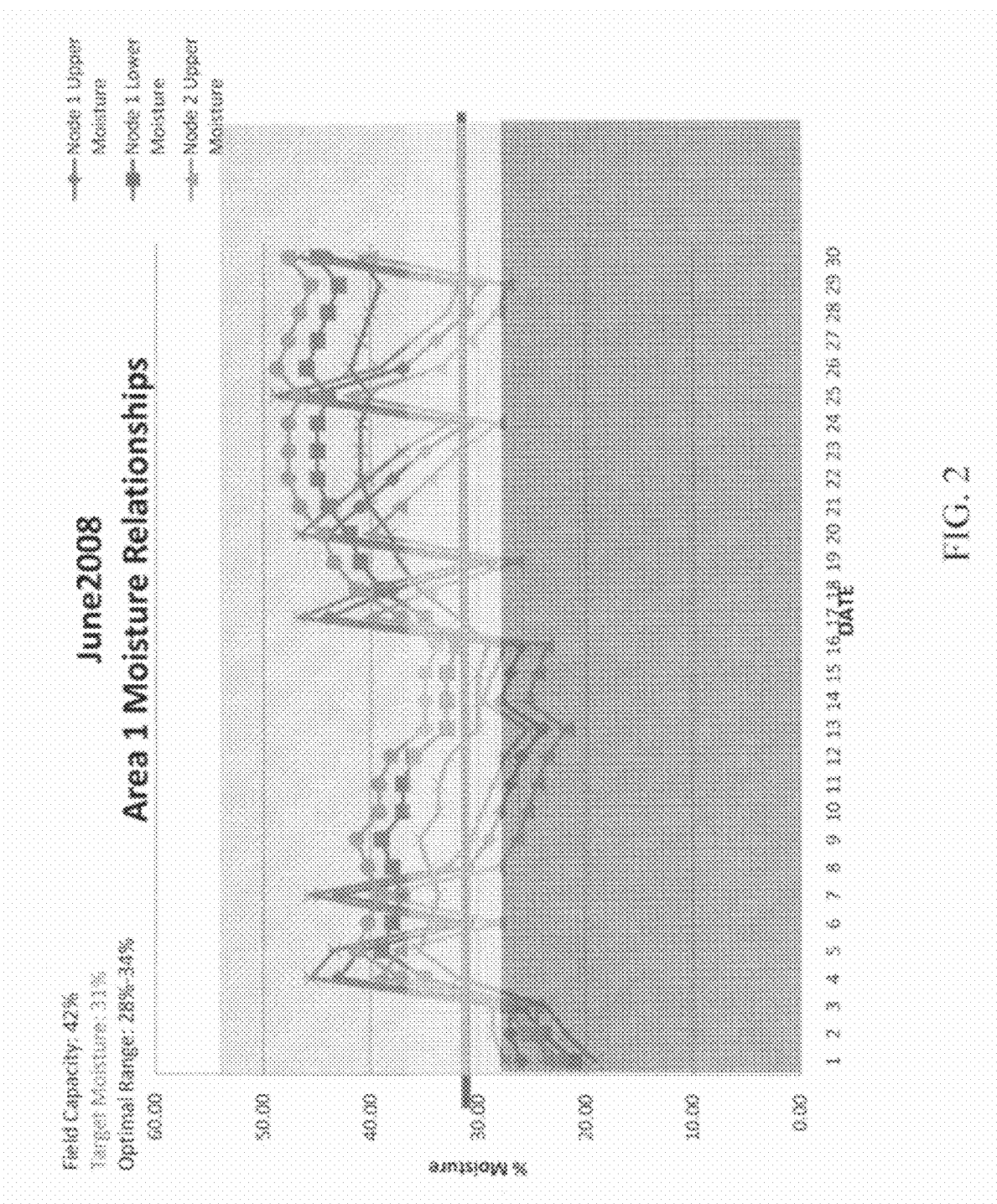
FIG. 2 is a graph of area moisture relationships.

FIG. 2 illustrates a chart that is useful for identifying various areas as they relate to the optimal or target moisture range. A description box that identifies the location, target moisture range, soil quality or any other pertinent data is important for easy reference to the end user.

An Upper/Lower Moisture Variance is preferably measured with soil moisture sensors. The formula is Upper Moisture %/Lower Moisture %. An index value is determined by dividing the upper moisture value by the lower moisture value in real time: 1.0=uniform moisture, >1.0=upper is more wet then lower, <1.0=lower is more wet than upper. This gives a real time view of how the soil's moisture value changes throughout various depths. Ideally a uniformly wet soil throughout the active rootzone is desired. The system 20 allows an operator to alter watering based on real-time inputs to meet to save water, maximize plant health and performance, and reduce moisture-induced stresses such as plant decline and disease.

Figure 3:
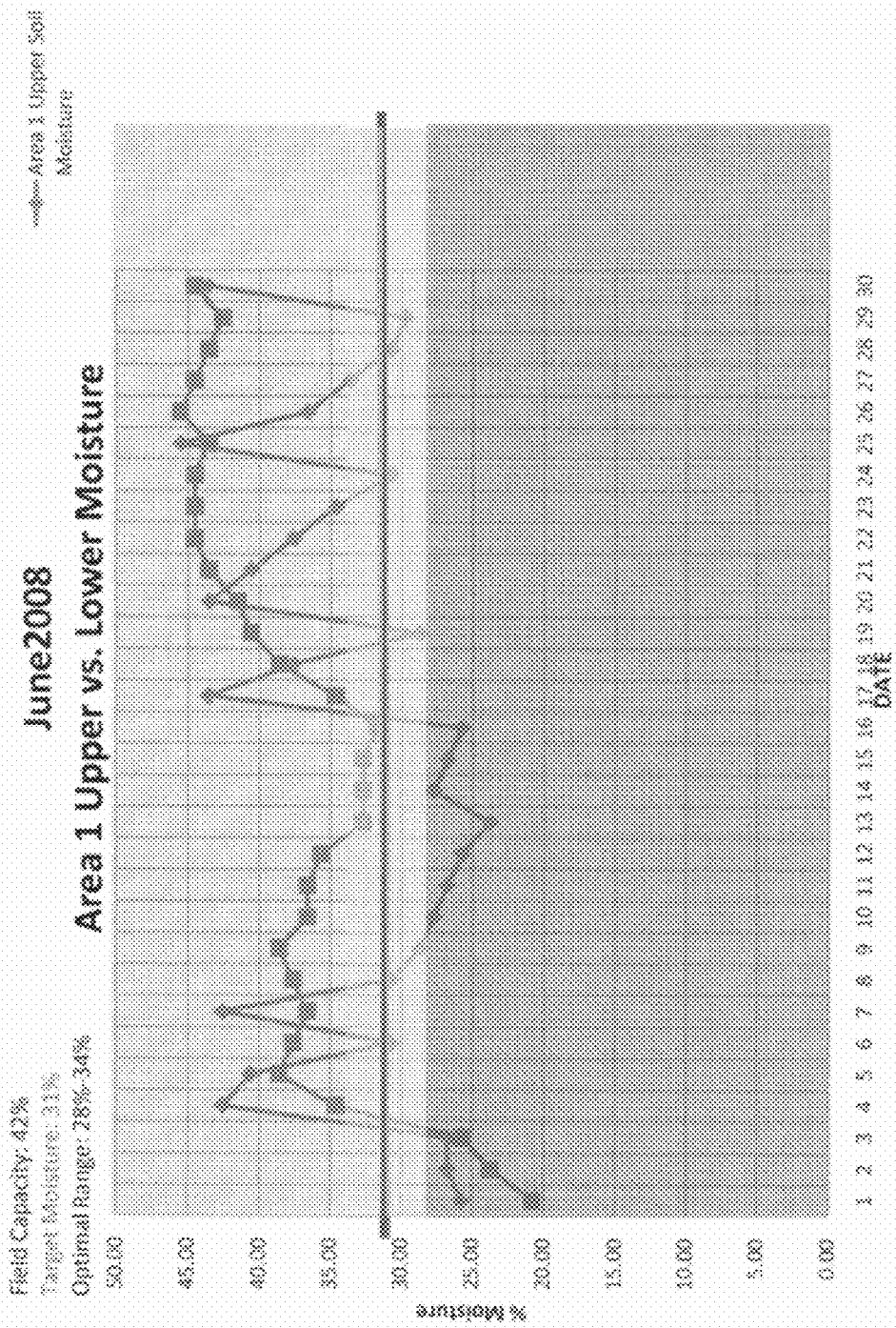
FIG. 3 is a graph of an area's upper soil moisture and lower soil moisture.

FIG. 3 illustrates the area's upper soil moisture versus the lower soil moisture. This chart illustrates where a particular area such as a green or football field falls in relation to its real time soil moisture levels compared to where it should be soil moisture levels. The optimal level is identified through soil tests, site assessment and historical data from the course. For instance, the system 20 knows that the history of the course is to water frequently where the moisture level is considerably above optimum. To prevent rapid plant decline, the system recommends against drying the soil down overnight. The system 20 makes this recommendation despite the fact that the optimal range for that particular soil is to be much drier than what the operator is used to maintaining Identifying the porosity of a particular soil as well as its field capacity, allows for the system 20 to determine the optimal moisture range. Typically this falls somewhere in the range of 70% to 80% of field capacity. That would be the starting point. From there the system 20 reduces watering to maintain the moisture level in the optimal range . . . again clearly indicated by the graph. In typical conditions, most operators irrigate to move well above the optimal range. Then, the operators do not allow the area to dry down to the lower limit of the optimal range and start the overwatering process again. In a worse condition the soil is allowed to dry too much where it takes an abundance of water to rewet. In either case, too much water is being used.

By maintaining the moisture level within the optimal range, water usage is reduces and plant performance is optimized. More importantly the system 20 adjusts the level over time as the system 20 trains the plants to accept the "drier" conditions.

The system 20 also uses charts for EC and temperature. Additionally, having an EC chart along with EC data from an irrigation source is useful to develop salt load indexes for irrigation cycles.

Figure 4:
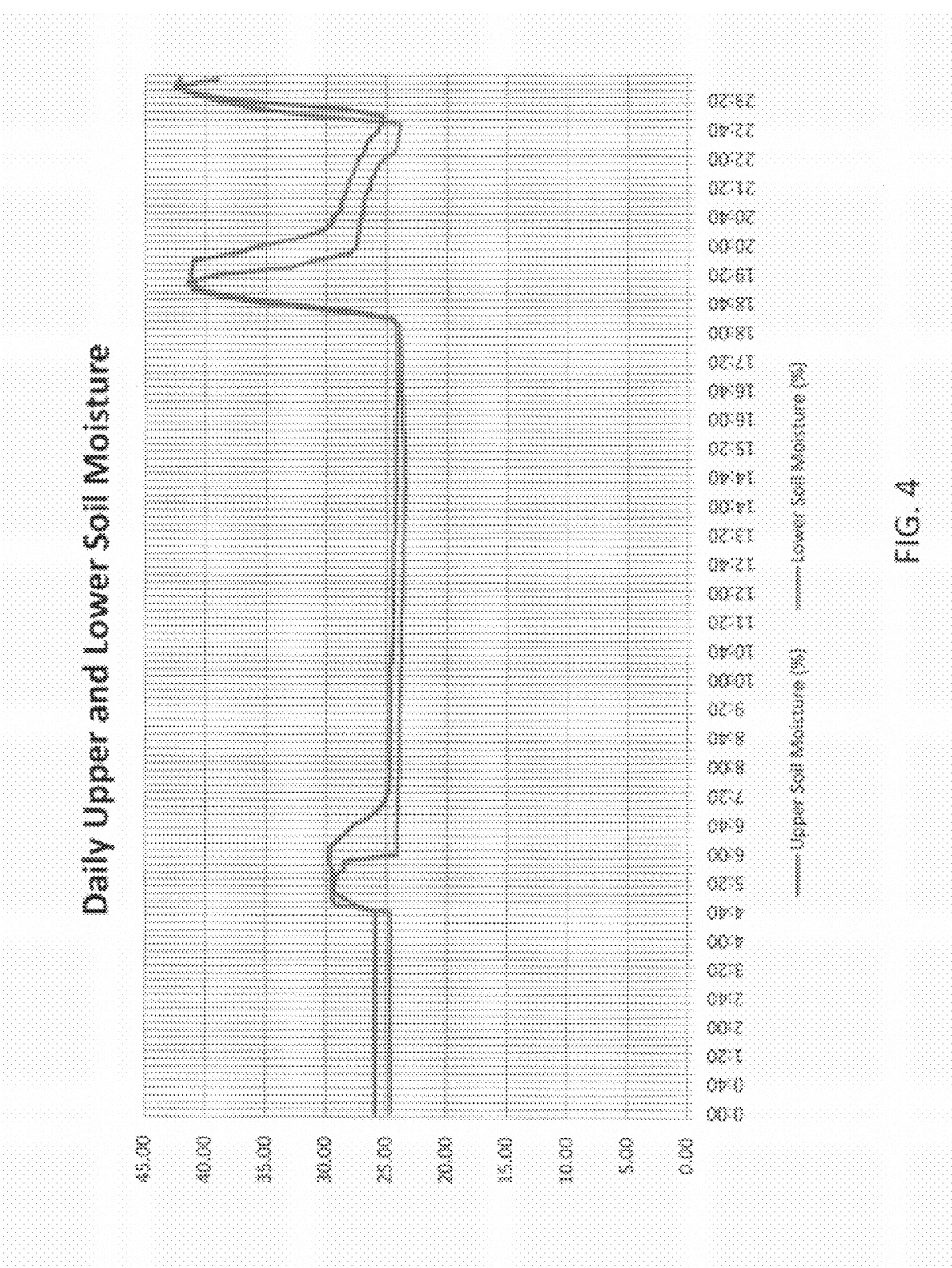
FIG. 4 is a graph of an area's daily upper soil moisture and lower soil moisture.

FIG. 4 illustrates daily upper soil and lower soil moistures. This chart simply shows the daily moisture patterns for upper and lower soil conditions in a particular area (green, fairways, field, etc). This is helpful for tracking irrigation cycles and how they affect soil moisture in a particular area. Organic matter which is highly variable throughout the year and throughout the soil profile, has a great impact on how water moves through the soil. These changes are monitored by the system 20 throughout the year and help adjust the practices to optimize the irrigation cycles.

In addition, one can use this chart to monitor the effectiveness of material applications. One example is with the use of wetting agents. By knowing how the water holding or releasing capacity of the soil changes in real time, the system 20 helps the user target these applications most effectively. The system 20 helps them understand these practices to make more informed decisions.

An Upper/Lower Temperature Variance is preferably monitored with a soil temperature sensor positioned within the node 21. The formula is as follows: Upper Temperature value/Lower Temperature value. An index value is determined by dividing the upper temperature value by the lower temperature value in real time wherein 1.0=uniform temperature, >1.0=upper temperature is hotter than lower temperature, and <1.0=lower temperature is hotter than the upper temperature. The system 20 provides real time indications of what plant stimulants exist at various levels of the rootzone. The system 20 uses this data to predict root stimulation versus leaf stimulation as each has separate inner temperature triggers. The system 20 also uses this information to indicate heat stress load on the plant or dormancy triggering. This is used to time cultural practices more precisely and accurately. Such cultural practices include seeding, fertilization, pesticide application necessity and timing, and many other plant physiological actions and reactions to temperature stimulants.

Figure 5:
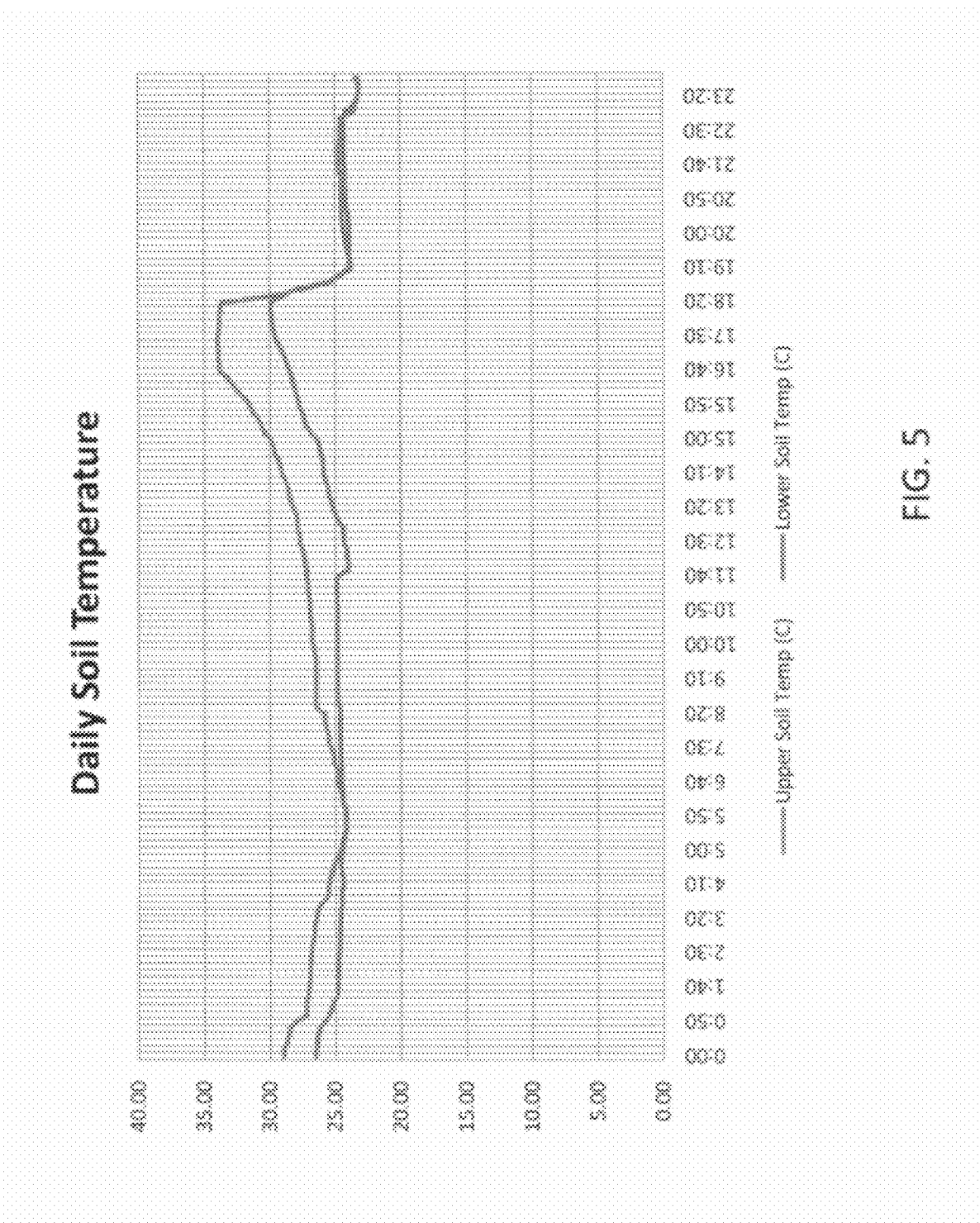
FIG. 5 is a graph of an area's daily soil temperature showing upper soil temperature and lower soil temperature.

FIG. 5 illustrates daily upper soil and lower soil temperatures. This simple chart shows the temperature fluctuations throughout a given day. The system 20 also shows a similar chart trending temperatures over a given amount of time that is user defined (1 week, 1 month, season, etc). Although heating a soil is somewhat impractical, there are many things that can be done to cool down a soil. For example, a simple one pass process using a spiking machine reduces the upper soil temperature enough to survive another summer day . . . or week. The system 20 provides the operator with an exact time to perform such a process by knowing the real time temperature conditions and the trends.

Figure 6:
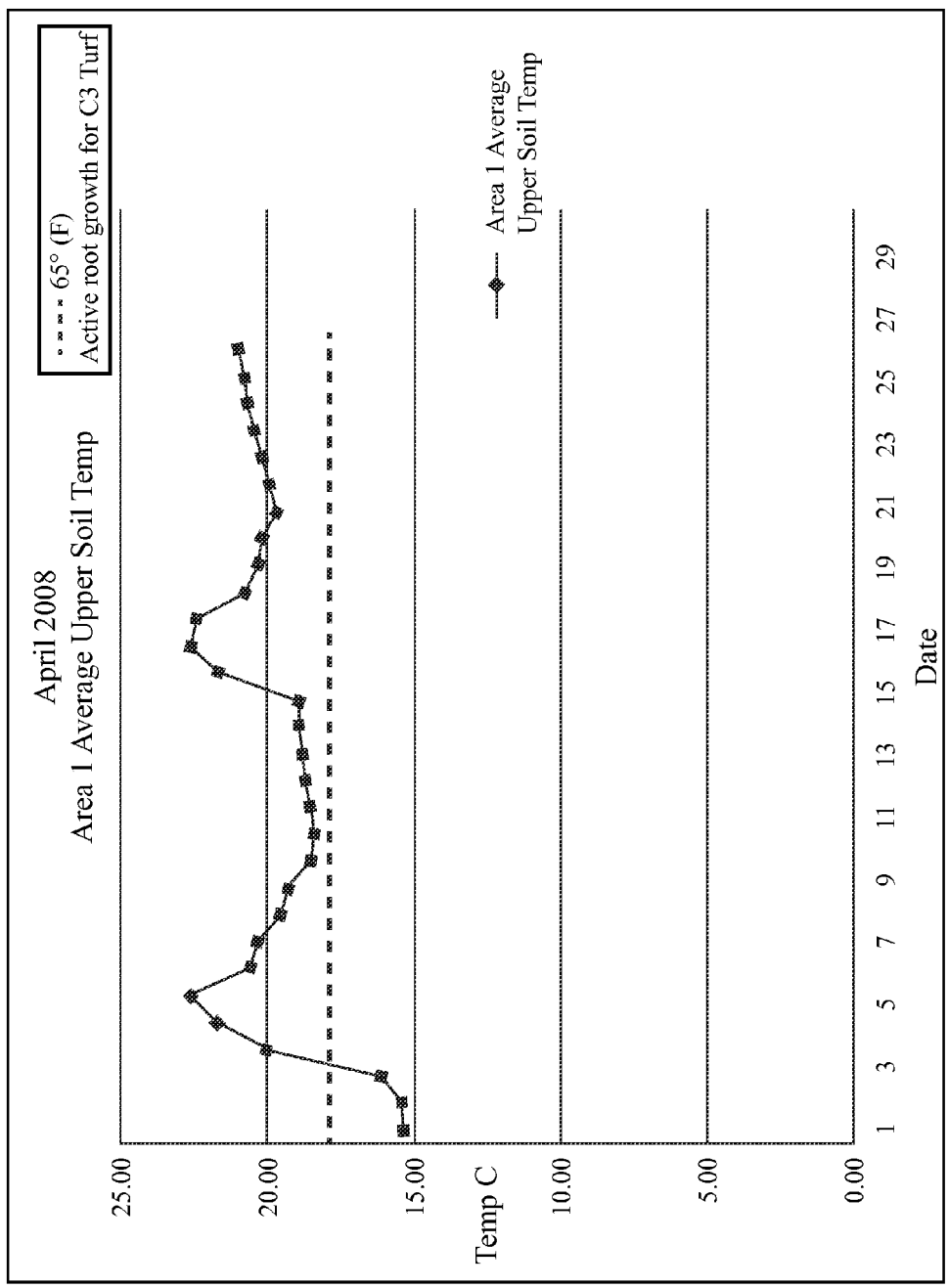
FIG. 6 is a graph of an area's average upper soil temperature.

FIG. 6 illustrates average upper soil temperatures. The upper soil temperature influences many parameters in turf management and other plant environments. The average upper soil temperature illustration has an indicator threshold line that shows the ideal temperature for active root growth in C3 turfgrass. Those skilled in the pertinent art will recognize that there are other options for this graph which include showing the upper limit of a particular process (like root growth) or having the ability to easily adjust the threshold line to accommodate a multitude of other processes (shoot growth, stress development, nitrogen release from organic matter, etc).

Figure 7:
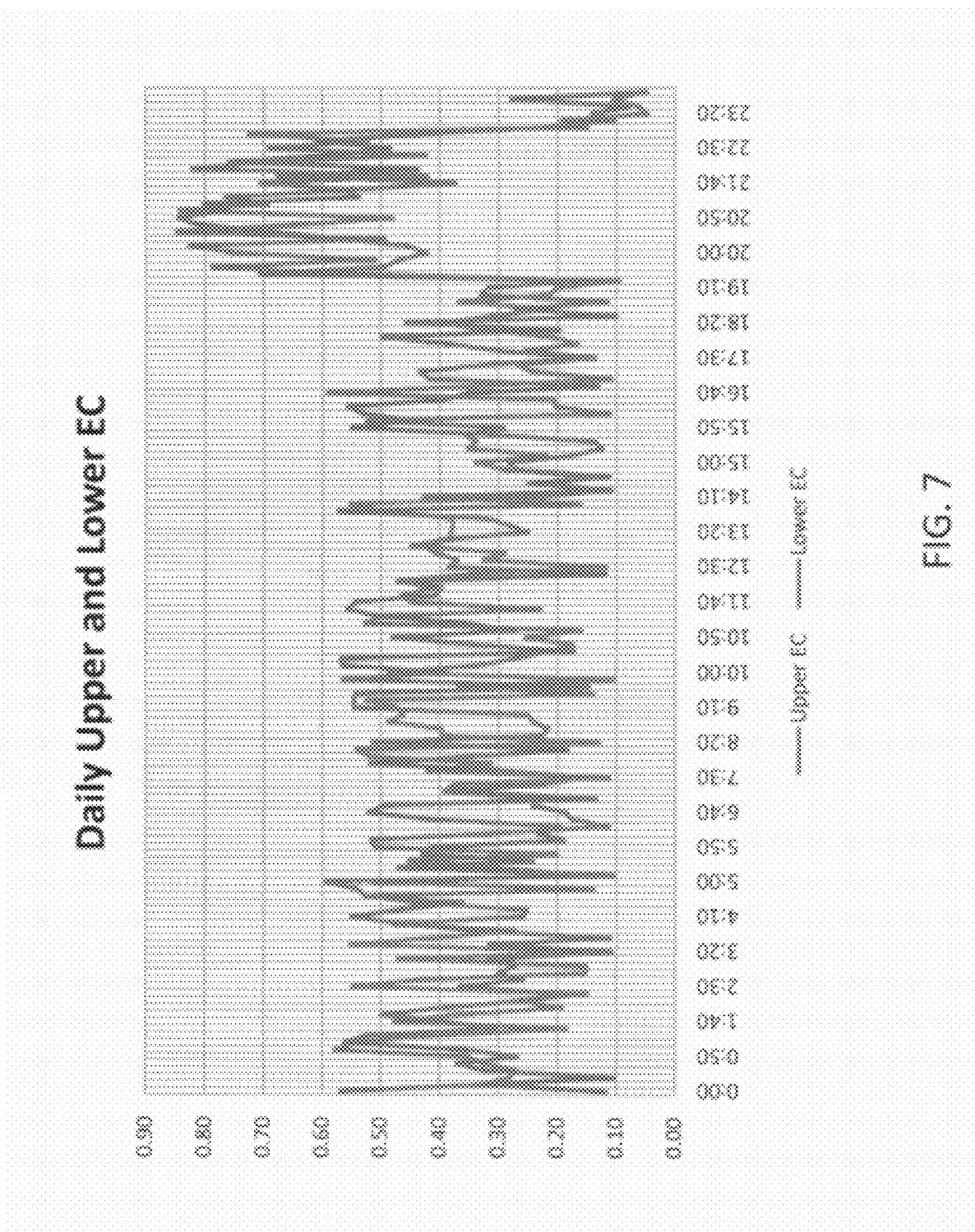
FIG. 7 is a graph of an area's upper soil EC and lower soil EC.

FIG. 7 illustrates daily upper and lower EC. Monitoring upper and lower EC on tight intervals is helpful particularly when monitoring sites with high salt loads (coastal, effluent, reclaimed water, etc). Showing a regression line indicator is probably more useful as it is more of a trend line rather than the actual data bouncing around as it does in the soil. One interesting thing about EC data is that providing inputs from an irrigation source (or fertilizer application) to the system 20 allows the system to make predictions of nutritional activity in the soil possibly caused by release of nitrogen from microbes breaking down organic matter. The system 20 also correlates EC levels with moisture levels to predict scaling and precipitation of solids from salts, all of which originates from monitoring EC levels in real time.

The Upper/Lower Salinity Variance is monitored with a soil salinity sensor. The formula is Upper salinity/Lower salinity. The index value is determined by dividing the upper salinity value by the lower salinity value in real time: 1.0=uniform movement of dissolved solids (salts) through the rootzone; >1.0=salts migrating in the upper rootzone; and <1.0=salts migrating in the lower rootzone. Salts are dissolved solids. The term "leaching" which is a very important environmental indicator refers to salts leaving a rootzone's bottom and possibly entering ground water or other off site areas. The real time monitoring of salts indicates what elemental stimulants exist in the active rootzone for plant growth, fertilizer release, and potential toxic buildup that will adversely affect plant growth. As salts migrate below the active rootzone then the potential for leaching exists at a much higher level. The benefit provided by the system 20 is managing salts most effectively in real time leading to stronger plant health and performance with minimized impact on the environment.

Figure 8:
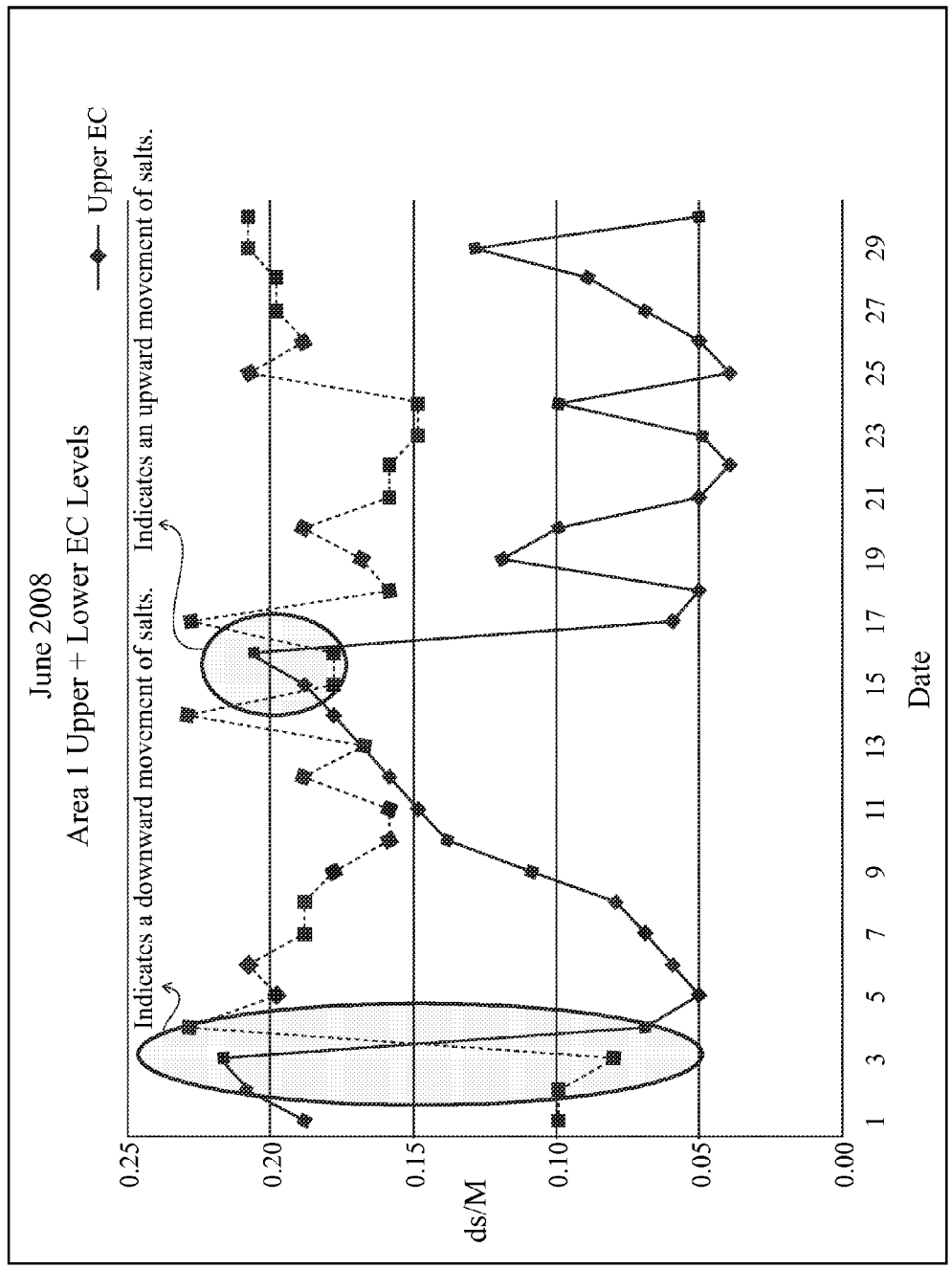
FIG. 8 is a graph of an area's upper soil EC and lower soil EC for June.

FIG. 8 illustrates upper and lower EC values over time. This chart shows upper and lower EC levels over time which should be user defined (month, week, season, etc). When one consistently places the upper sensor within the active root system mass (typically 2 to 2.5" for upper soil) and the lower sensor toward the bottom of the root mass (typically 3-5" for lower soil) then one has the ability to make many predictions based off of soil conditions. This chart shows the movement of salts from upper to lower or lower to upper. One can see downward moving traits (leaching, deep root encouragement, etc) and upward movement (transpiration, high ET rates, potential salt deposition, etc). This type of monitoring is not limited to turf. For instance, this form of monitoring is used for storm water runoff monitoring sites where runoff could end up in water ways. The leaching of salts is shown through the profile and thus the pollution potential at any given time is known by using this form of monitoring. Those skilled in the pertinent art can see how this could help agencies define practices to better control this runoff or pollution through the soil. In a plant environment, this chart provides a visual of what is happening in the profile as it relates to upward or downward movement of salts.

The Moisture-Salinity Index is monitored using soil moisture and salinity sensors. A weighted average formula is utilized for the moisture salinity index. By identifying the optimal moisture and salinity levels for each soil and plant type, this index is weighted appropriately to show where the combined variables of moisture and salinity vary from what is optimal. The user of the system 20 sees in real time where a problem exists. There is a strong relationship between available moisture and salinity since by definition salinity conductivity (what sensors of the system 20 measure) is a measurement of dissolved salts (in solution). Without solution, or moisture, there is no salinity measurement as the salts precipitate out as fine solids in the soil. As solution frees up (or moisture levels rise) the salts return into solution and salinity levels rise. Thus, there is an optimum combination for every soil and plant type which the system 20 identifies clearly with real time measurements.

The soil moisture-precipitation-evapotranspiration index is preferably monitored with a soil moisture sensor 33 set at ambient temperature. A weighted average formula is utilized for the soil moisture-precipitation-evapotranspiration index. Without real time soil moisture readings, industry decisions regarding how much to irrigate are done by feel, sight and estimates from ambient (above ground) data. The most commonly referenced variables include precipitation measurements and evapotranspiration (ET) which is a formula that estimates how much water is lost from plant transpiration (the movement of water through the roots, up through the plant and out of the leaves) and evaporation (the change of water from a liquid to a gas). The ET formula most utilized today is the Penman-Monteith ET calculation which has been in use for decades. The system 20 takes real time soil moisture conditions which are what the plant sees at any moment (a much more precise indicator of available water or the need for water) to precisely indicate how to irrigate the land area most effectively. The system 20 further defines this need by correlating the ET calculation, precipitation and actual soil readings to effectively and precisely irrigate most effectively. The ET calculation also estimates the soil type so it truly is an estimate that only real time soil monitoring can adjust appropriately.

Figure 9:
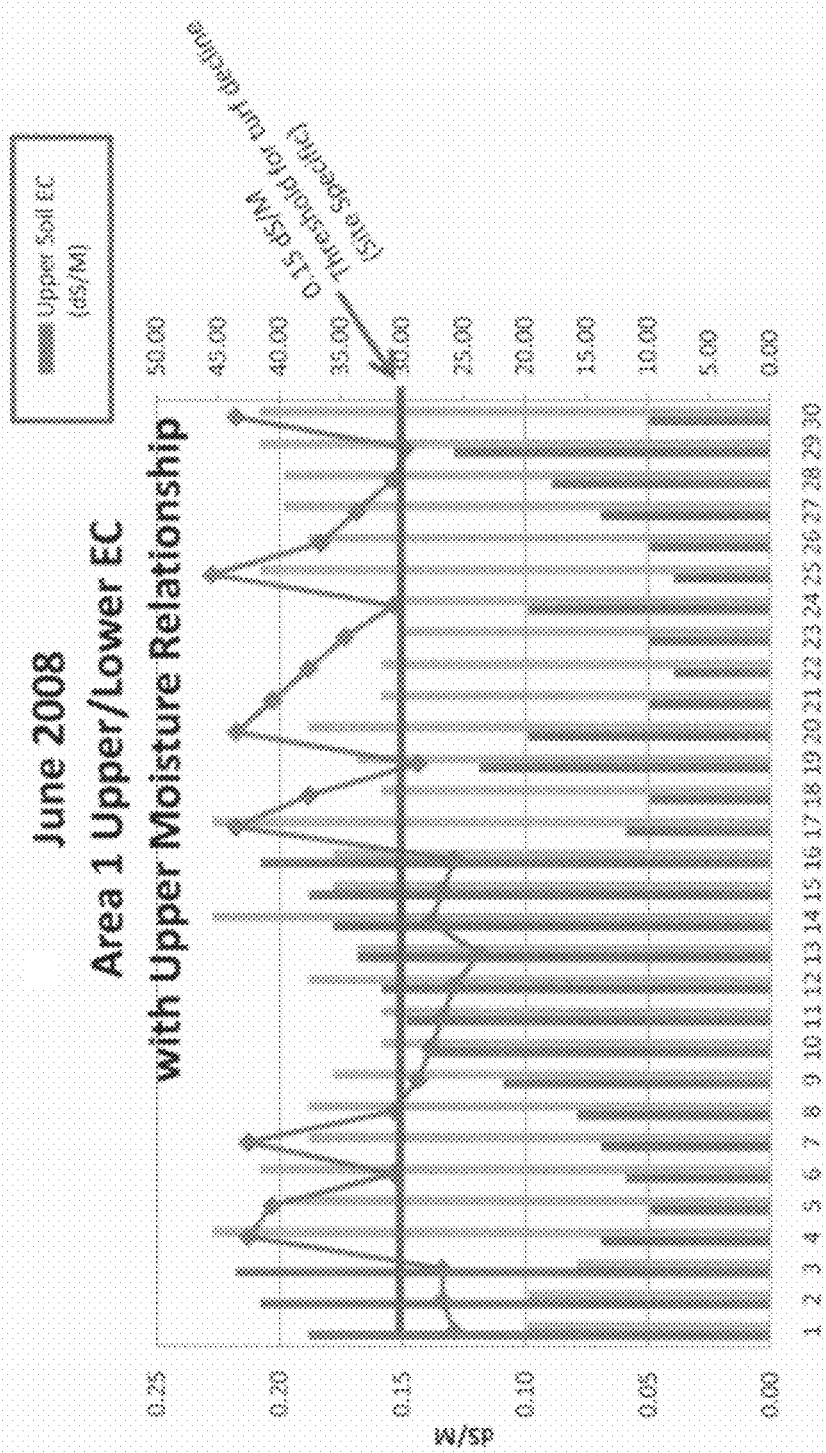
FIG. 9 is a graph of an area's upper soil EC and lower soil EC versus upper soil moisture.

FIG. 9 illustrates upper and lower EC values in relation to soil moisture. This chart simply illustrates how the salts in the profile relate to soil moisture. This is helpful when considering the practices of a particular facility and how they relate to the salt and moisture management of a soil. For instance, if there is a rapid decline in a particular area that is being monitored, and system 20 knows the exact combination of salts and moisture, the system 20 sets this as a threshold so that the system 20 can better prepare for future practices. There is a delicate relationship between salts and moisture. For example, a turf that handles a salt level of 0.32 dS/M with 24% moisture is not able to handle the same salt load with 17% moisture . . . or vice versa. This chart provides the system 20 the ability to monitor the trends easily and make suggestions to better manage the salts and/or moisture.

Figure 10:
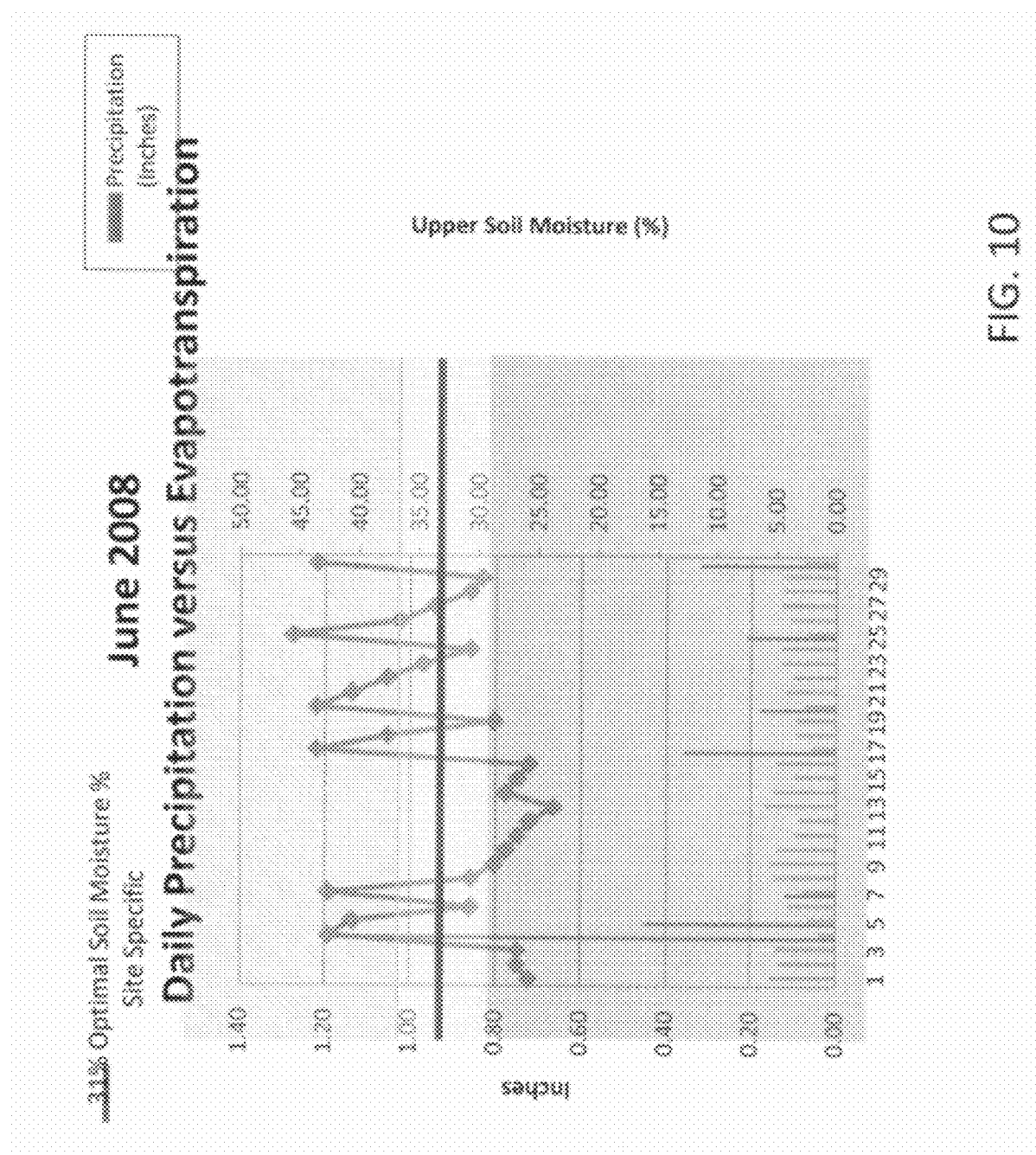
FIG. 10 is a graph of daily precipitation versus evapotranspiration.

FIG. 10 illustrates daily precipitation versus evapotranspiration. This chart illustrates trending of soil and ambient conditions. Evapotranspiration requires variables of solar radiation, precipitation, air temperature, wind and relative humidity in addition to site data such as latitude, elevation above sea level, etc. Evapotranspiration is a measurement of estimated water loss from plants and soil through transpiration (the movement of water into the roots, through the plant and out of the leaves) and evaporation (the conversion of water to gas). The meteorological data is taken automatically from a MET station (which also logs leaf wetness) or input from another weather data source such as a regional monitoring station or other source. This is one way that the system 20 inputs data from a weather data source.

There is a great benefit to being able to compare ambient data with soil data as indicated by the charts. The current chart logs precipitation and ET and is used to help adjust irrigation cycles. ET calculations are typically based off of a 50 year old scientific formula that is quite accurate but does not consider real time soil conditions. The system 20 monitors soils in real time and sees how those conditions compare to the accepted ET calculation so that an operator can make more defined adjustments to irrigation practices as they truly relate to optimal plant health and performance.

Figure 11:
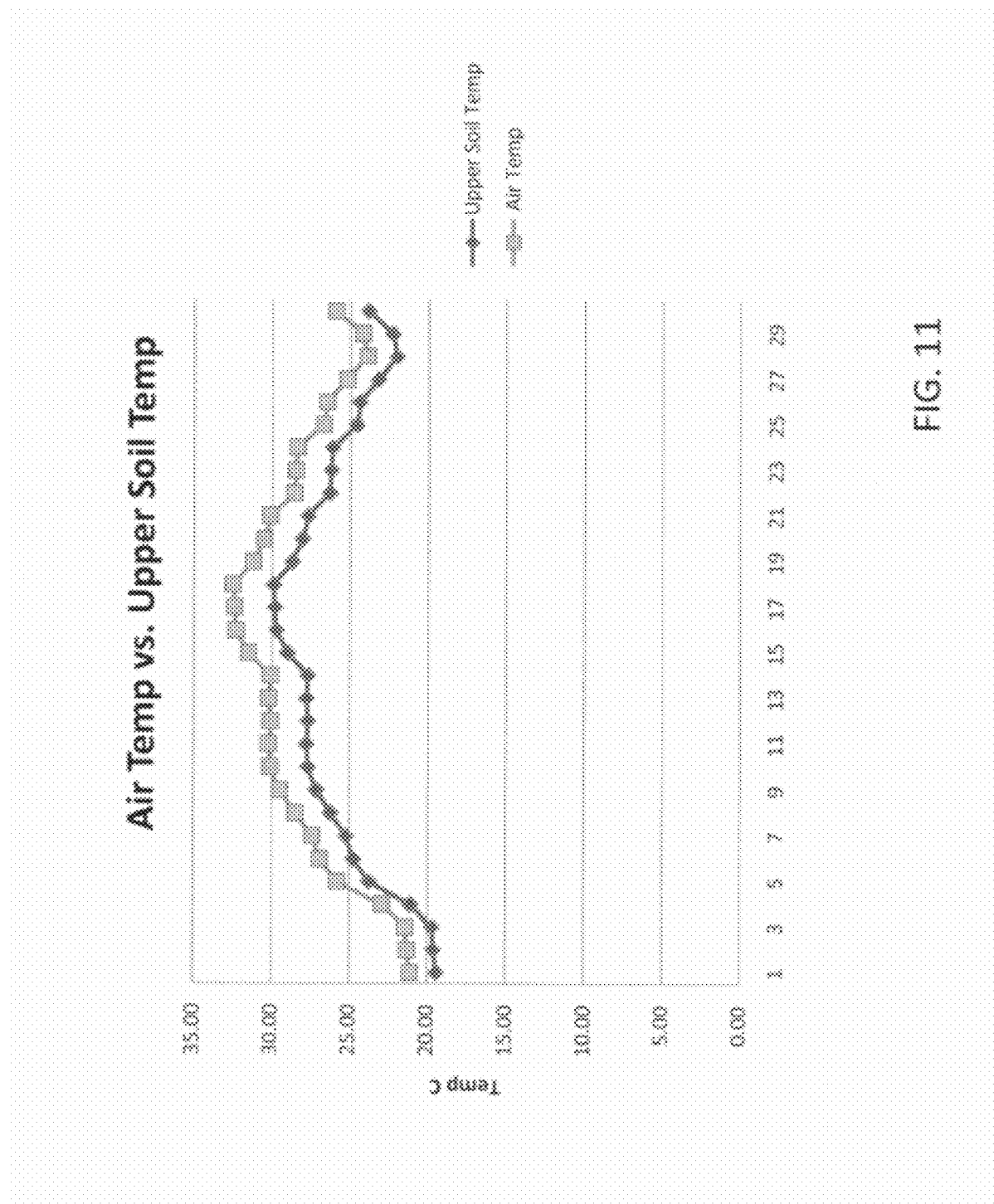
FIG. 11 is a graph of air temperature versus upper soil temperature.

FIG. 11 illustrates air temperature versus upper soil temperature. While this chart shows a similar curve with air temperature and soil temperature, this is often not the case. For instance, since water conducts heat very well soils are hotter than air in the summer. While turf can survive air temps above optimum levels, this is not the case with soils as there is a direct relationship between root and shoot loss to above-optimum soil temperatures. The system 20 accounts for several indicators and thresholds, and the chart of FIG. 11 gives a clear illustration of soil temperature as it relates to the ambient conditions.

When soil temperatures do exceed air temperatures, one typically sees great respiration stress in turf in the summer but extended root development in fall/winter/spring seasons. In transitional stands of turf, this data can be very useful or timing selective herbicide or nutritional practices designed to promote a particular species.

The Air Temperature-Upper Soil Temperature is preferably monitored using a soil temperature sensor 33. In real time with an active on site weather station, the system 20 uses its real time soil monitoring to compare air temperature with soil temperature so that the user can easily see how air temperature affects the plants. By having a further understanding of how ambient conditions affect in-soil conditions the user makes more informed decisions more accurately and precisely in a more timely manner. In addition, if there is a region of a facility that is lacking in plant performance or yield, adjustments are made to help the ambient conditions improve the soil conditions. An example is a situation where undergrowth has crowded a wind corridor that no longer allows free air to move across a site and thus cool the otherwise dense stagnant hot humid air that exists.

Figure 12:
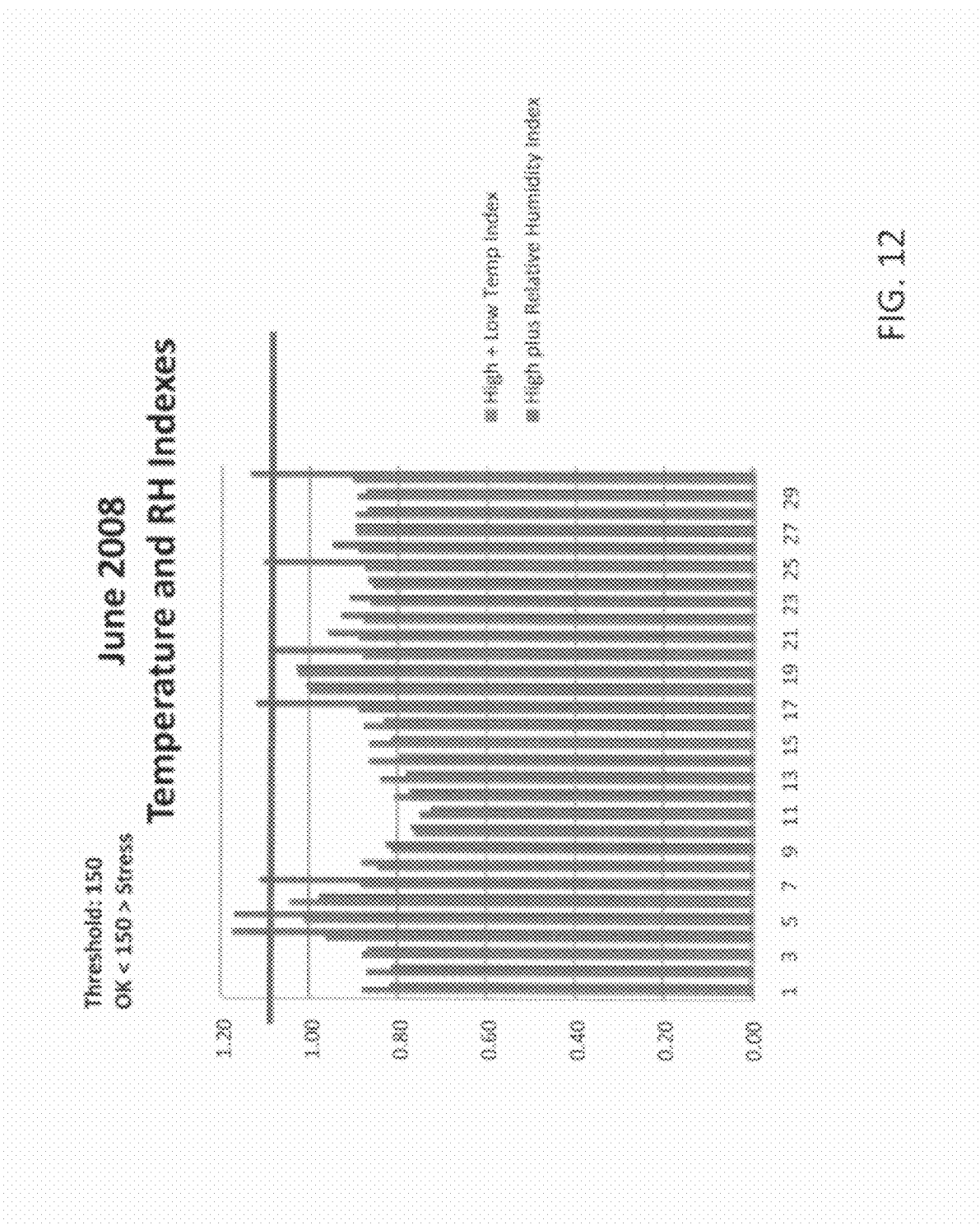
FIG. 12 is a graph of temperature and relative humidity indices.

FIG. 12 illustrates temperature and relative humidity indexes. Two indexes used in turf management include the high/low temperature and high temperature+relative humidity indexes. For C3 turf, when the system 20 takes the daily high temperature+low temperature (F) or the daily high temperature+the daily relative humidity (whole %) and gets a number that is equal to or greater than 150, the turf is under great stress. With real time monitoring the system 20 knows the relation to this index at any given time. More importantly, the system 20 adjusts this threshold easily over time. For C4 turf, a threshold of 165 is more appropriate than 150.

The threshold setting doesn't matter as long as it consistent at a particular site. This chart shows an index in relation to the threshold setting. The red line is the indicator threshold of 150 and the bars tells whether the threshold has been crossed. The charting aids the system 20 in stress management practices.

Figure 13:
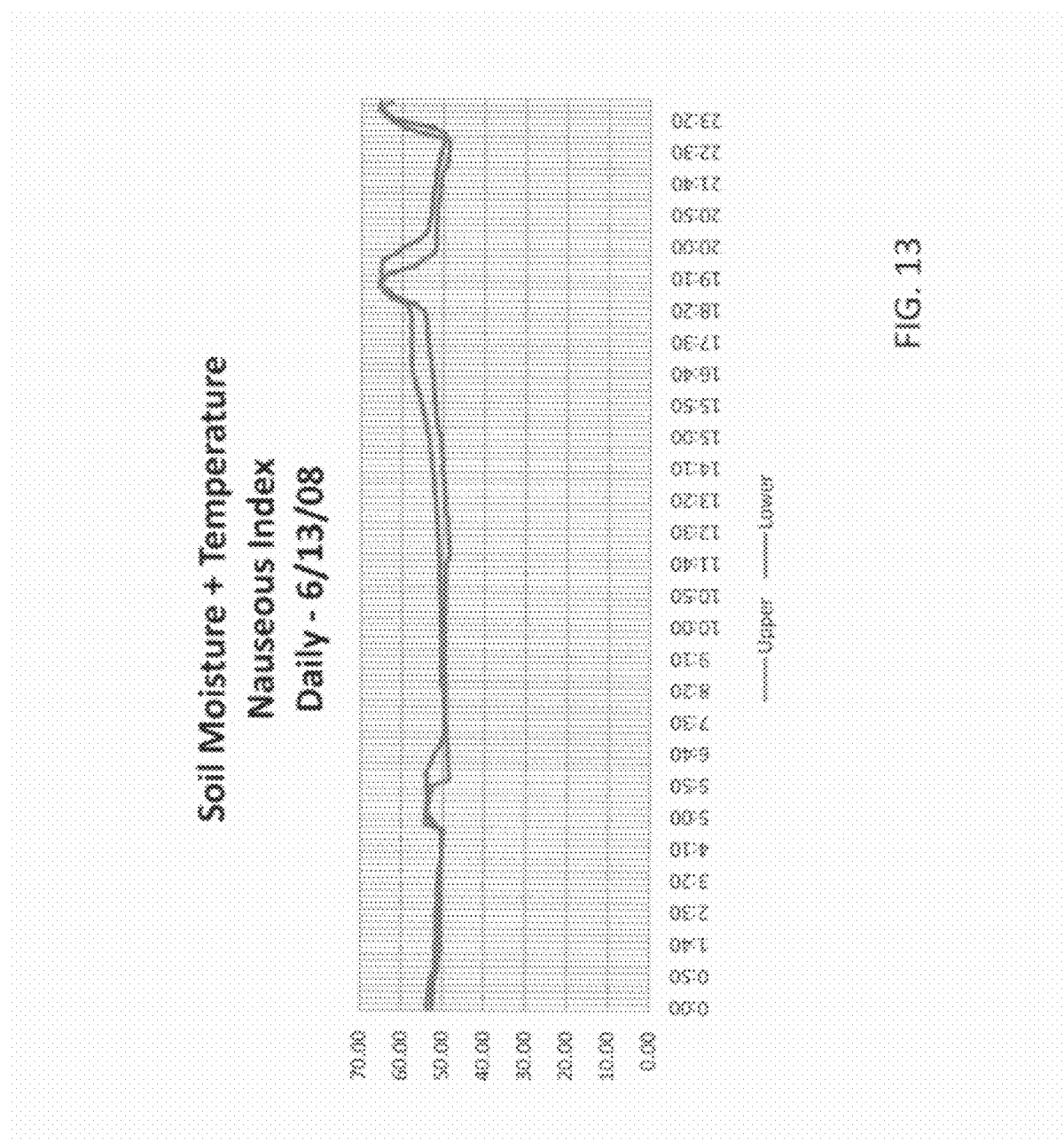
FIG. 13 is a graph of soil moisture and temperature.

FIG. 13 illustrates soil moisture plus soil temperature. This chart is another illustrative stress indicator. There is a breaking point in every turf system where the combination of soil temperature and soil moisture causes turf to decline. The system 20 identifies that level based on input from the user and monitoring over time. Once the level is set, the system 20 shows the user where the soil is in relation to the threshold at any given time. Using this particular chart with showing daily values, the system 20 defines exactly where an operator needs to be and when with a syringing hose, a fan or one of several other practices designed to reduce stress including nutritional inputs.

Figure 14:
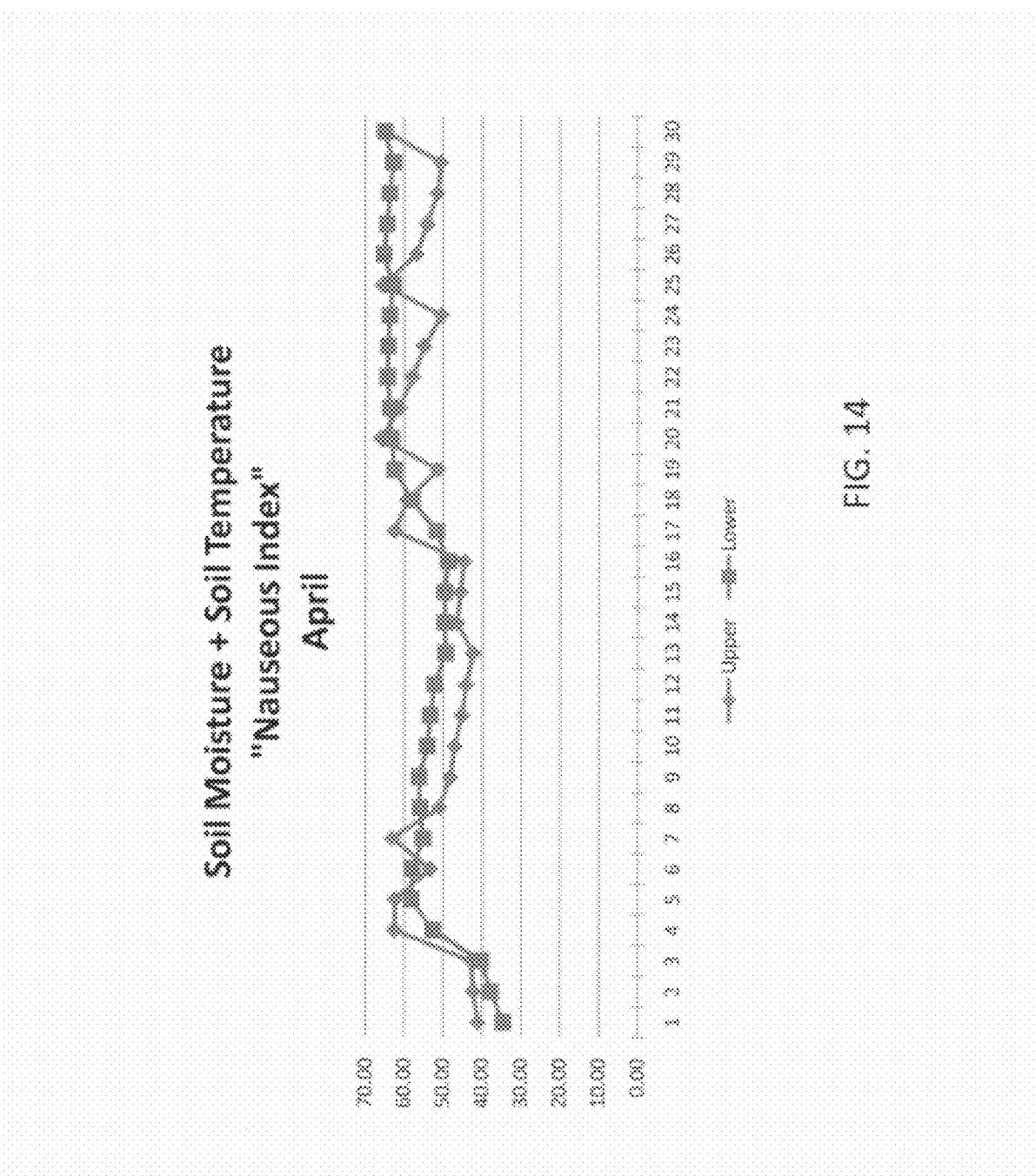
FIG. 14 is a graph of soil moisture and temperature.

FIG. 14 illustrates monthly soil moisture and soil temperature. This shows the upper/lower nauseous index trend over a given period of time such as a month as is the case here. Again user definition of the time period as well as a description box showing the threshold and other key data is important.

Figure 15:
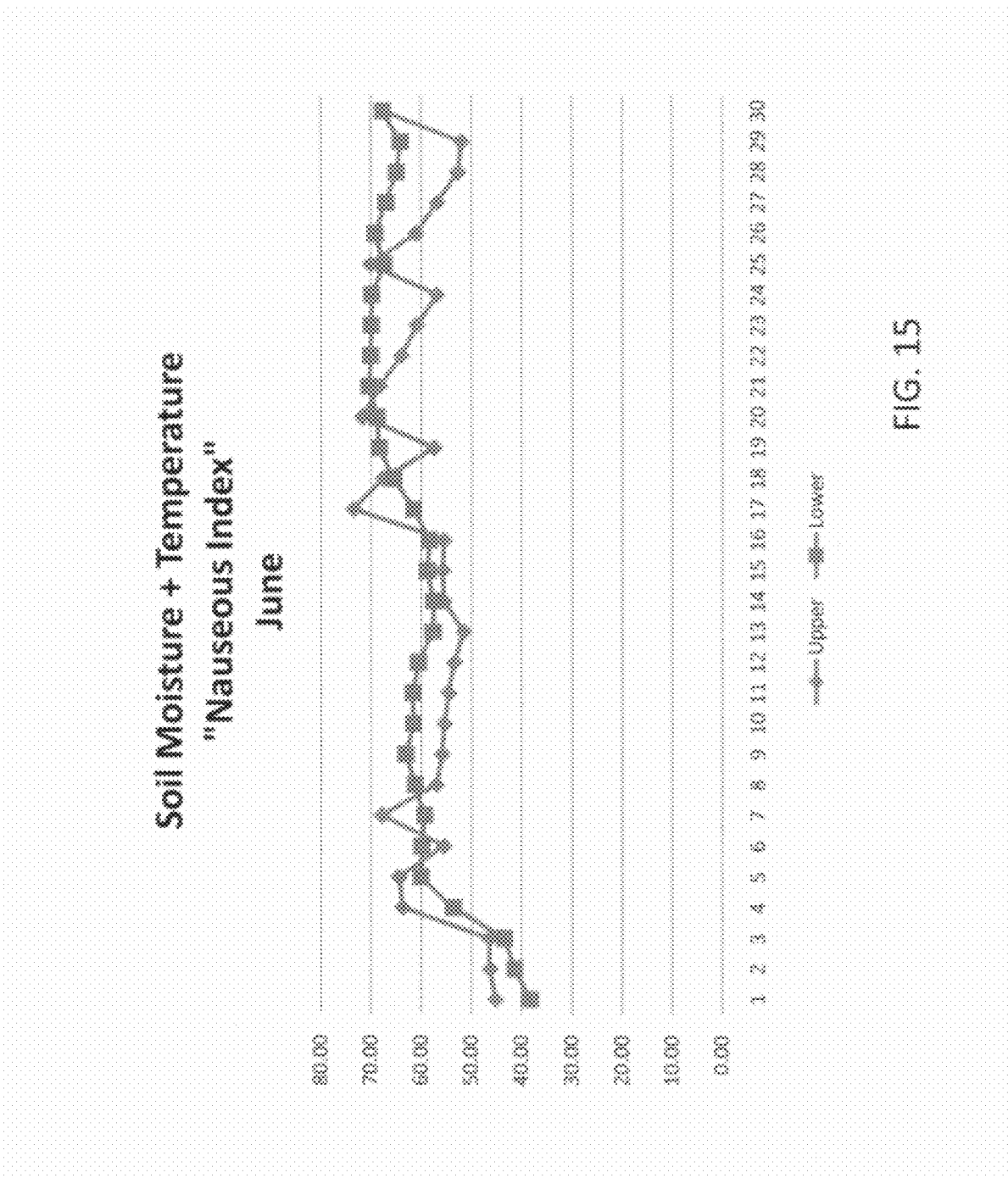
FIG. 15 is a graph of soil moisture and temperature.

FIG. 15 illustrates monthly soil moisture and soil temperature for a subsequent month. Showing a regression or trend line for each month overlaid with each other may be useful.

The Soil Temperature-Humidity Indexes is preferably monitored using a soil temperature sensor at ambient temperature. A weighted average formula is used for this index. For every plant there is a threshold tolerance of both temperature and humidity. When combined the effects on turf are far greater. Every plant has a tolerance level that varies from other parts of the same facility and from other facilities, even if it is the same plant and soil type. By combining the ambient temperature and humidity with the soil's site specific temperature and moisture levels the system 20 defines a weighted average formula specific to that site, plant species and soil to indicate when the threshold is approached which will result in plant decline. For example, in the Mid-Atlantic region of the United States where cool season grasses are grown such as bentgrass and ryegrass and bluegrass, these grasses are very prone to decline from summer heat/humidity combinations. The symptoms that occur from this decline typically show up 72 hours after the "trigger" occurred internally in the plant. The system 20 indicates the conditions present for that stress "trigger" well enough in time for the operator to make appropriate decisions to offset stress and avoid plant decline.

The Soil Temperature-Moisture Index is preferably monitored using soil temperature and moisture sensors 33 of the system 20. A weighted average formula is preferably used for this index. The results of this index indicate where the user is in relation to a site specific temperature-moisture combination stress load within the soil. Similarly to the explanation above, again, there is a combination of temperature and moisture that greatly affects turf and plant performance, growth and health. Typically if a plant is not growing it is on the edge of or it is declining or even dying. The system 20 measures soil conditions in real time so that key points where the decline initiates (long before the symptoms appear on the surface) are identified so that more precise decisions are made to improve the plant and soil health to prevent the decline.

Figure 16:
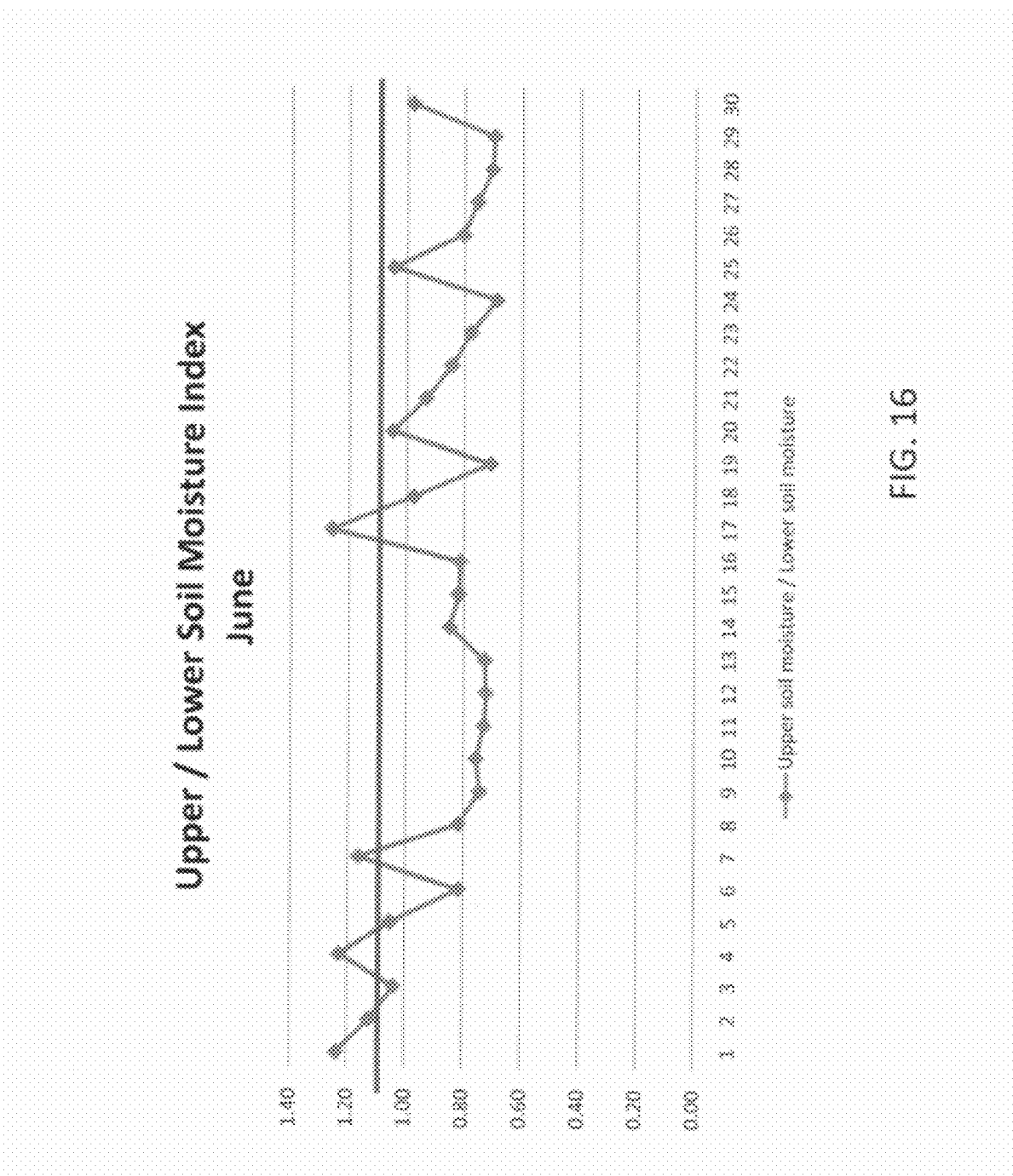
FIG. 16 is a graph of upper soil moisture and lower soil moisture index.

FIG. 16 illustrates an upper/lower soil moisture index. This chart shows the relationship of the upper soil moisture to that of the lower soil moisture in the given area, such as Green 3 or Fairway 7. Again, consistency in sensor placement is important, to have one in the middle of the root mass and one toward the bottom of the active rootzone. The red line indicates an index reading of 1.00 which is where the upper soil moisture is the same as the lower soil moisture. Climbing above 1.00 means that the upper profile has a higher moisture % than the lower profile. Falling below 1.00 then the lower profile would have a higher moisture % than the upper profile.

Since it is very difficult to re-wet a dried out lower profile, knowing where the entire profile is with regard to moisture percentage is a very good indicator of how deeply to water. As a soil dries down below its field capacity (the point where the soil cannot hold any more water without losing it to gravity), capillary movement begins to increase. Capillary movement is the movement of water in multiple directions due to cohesive forces to water, soil particles, roots and other components as well as its ability to move upward due to the same forces or in response to transpiration "pull." The system 20 warns when a lower profile is nearing drying out so as to prevent a loss of a tremendous "pool" of available moisture that the plant depends upon in times of stress. By keeping the profile properly moist throughout, the system 20 greatly reduces water inputs since the soil does not need to be rescues with overwatering practices.

The Soil Degree Day Indexes is preferably monitored using soil temperature, moisture and salinity sensors 33. Weighted average formulas are used for these indexes. There are a multitude of indexes that the system 20 developed for target specific issues so that a user knows where he is in relation to that target at any time through real time soil monitoring. Growing Degree Days have been around for a long time as a standard measurement of biological clocks for timing the activity of certain organisms. However, these measurements have been based on ambient conditions by taking the average temperature each day and subtracting some base temperature that is known to trigger the development of a certain biological organism . . . typically used in insect development timing. Since one can theoretically measure growing degree days in this fashion quite rapidly due to acute weather changes, it is a very vague estimate for determining biological activity in the plant or its surrounding environment. The system 20 measures real time soil conditions. Since the plant is influenced more so by soil conditions and the soil is not as pone to acute changes from the weather, it makes for a much more accurate indicator of plant affected variables. The system 20 developed multiple degree day indexes for common issues that affect plants. These include: root stimulation, leaf stimulation, multiple disease pathogens, insect development, heat stress load, dormancy triggering, and most importantly customized models based on site specific stresses. In this later case, the system 20 identifies the stress, measures the present and leading conditions leading up to it and then customizes the degree day model to indicate to the user in real time where the conditions are in relation to this stress at any time. This is all contingent on real time wireless soil sensing that is representative of the site. These indexes can utilize any of the soil variables we measure or any combination of them.

Figure 17:
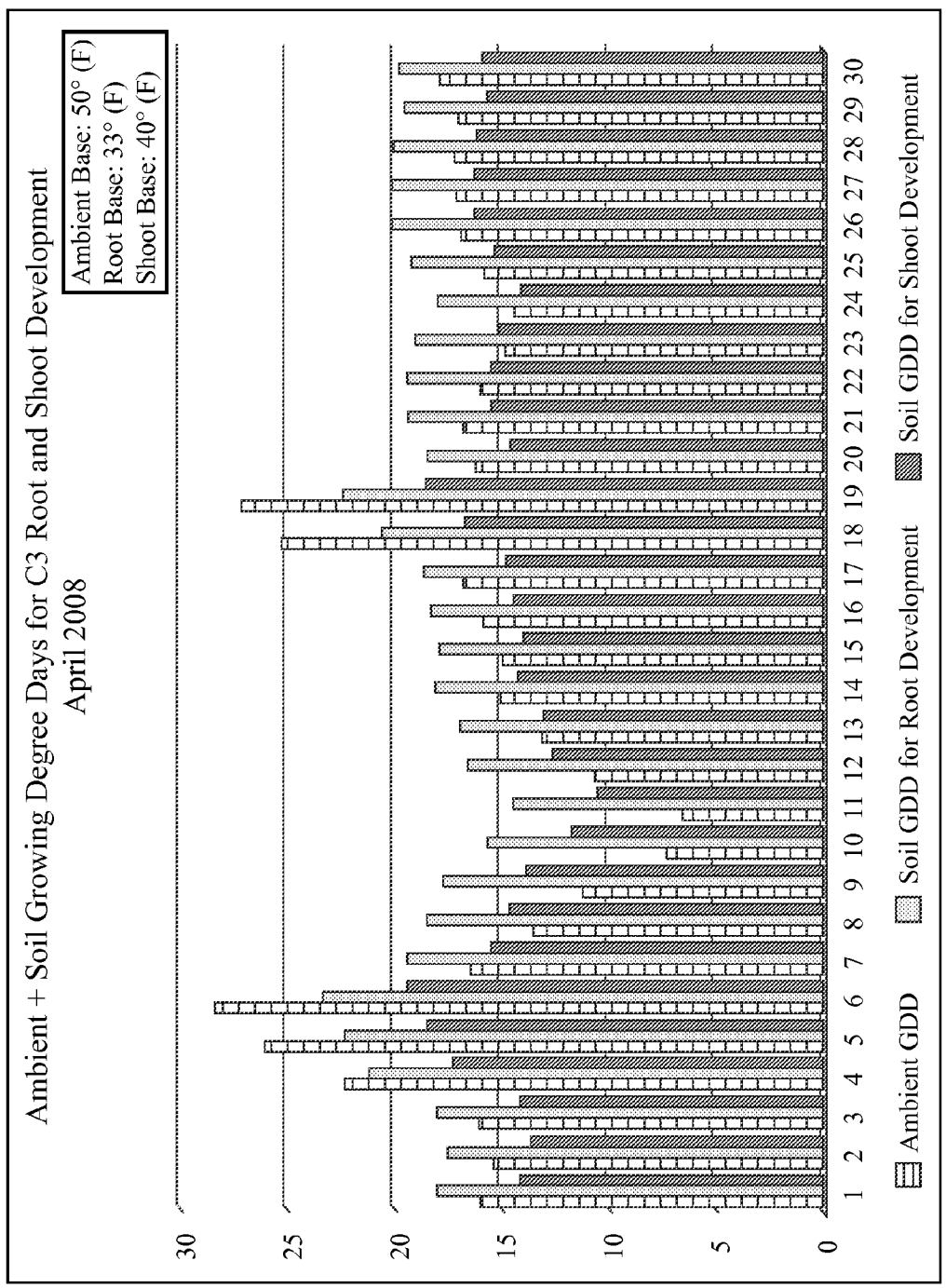
FIG. 17 is a graph of ambient plus soil growing degree days for C3 root and shoot development.

FIG. 17 illustrates ambient plus soil growing degree days for C3 root and shoot development in April. Growing degree day (GDD) models have been used for a long time but up until now they are primarily based on ambient (above ground) conditions. However, much research has been done to show critical plant physiological activities and organism responses to soil temperature. The system 20 has the ability to offer real time degree day models for a multitude of responses.

To accurately calculate traditional growing degree days on a site, the system 20 preferably uses weather variables at that site, most importantly air temperature. For soil GDD the system 20 only needs soil temperatures. Growing degree days are calculated by setting a base temperature threshold. The most commonly used base temperature across all grass species is 50° F. (10° C.). GDD are calculated by taking the day's highest temperature and adding it to the lowest temperature, dividing by 2 and subtracting the difference between that result and the base temperature. If the number after adding and dividing is equal to or less than the base temperature then "0" degree days are calculated for that day. As each day passes the degree days are added to each other and accumulated over time. Biological entities all respond to specific degree days accumulations. The argument in science is when to start calculating the degree days? For insects it seems that they should start on the $1^{st}$ day of the year. For many plant specific responses, many will start it on March $1^{st}$. It doesn't really matter when an operator starts recording the data as long as it is consistent year after year for comparison. It makes the most sense to simply start it on the $1^{st}$ of the year so that a total GDD YTD at any time, and an operator can draw conclusions from that data year after year.

For example, last year in the middle of April there were only 38 accumulated GDD. But this year there are 78. Obviously the needs of the turf were far greater earlier in the year this year so if an operator followed the same nutritional practices as last year for instance there would probably have very hungry turf this year. This is just one vague example but nonetheless it shows an available trending tool based off of GDD.

Where the system 20 provides a tremendous advantage over others is that the system 20 offers real time soil GDD through wireless monitoring. Since soils do not react to climatic variance as easily as ambient conditions do, the system 20 has the ability to utilize a more stable and predictable model. An observational study was conducted with sensors of the system 20 that were set up to look at *Poa annua* seed head emergence based on GDD. *Poa annua* seed head management is critical for early season putting conditions and a lot of money is paid on trying to suppress them. The problem is that most of the products used to suppress the seed heads have an optimal target range of 48 hours meaning they have to be applied within 48 hours of seed emerging from the boot (or sheath) of the turf otherwise the results are compromised.

The prior art GDD model showed that seed head emergence (based off of ambient GDD) was between 25 and 50 GDD, which is a large window. In the study, a current model of the system 20 was used as well as soil data to log where the soil was in relation to the emerging seed timing. What was found was that in every instance the window of GDD calculated on soil variables alone had a variance across all treatments of less than 8 GDD. The ambient GDD over the same treatments had a range similar to what was previously documented by others. This would easily allow a user to better manage his/her treatment for seed head control and get within the 48 hour window thus save excessive applications or reduced results from those applications.

GDD can be used for many things in turf and plant management. These include root growth, shoot growth, seed production, germination, disease pathogen development, insect development, tiller stimulation, accumulated stress load and others. The chart illustrated shows the calculated ambient and soil Growing degree days for root and shoot development of C3 turf. The base temperature is 50° F. for ambient GDD, 33° F. for root development since the roots begin to develop (in C3 Turf) sugars as soon as the soil begins to thaw, and 40° F. for shoot development. This bar chart relationship simply illustrates where each GDD is based off of the above variables. The system 20 adjusts the bases if wanted but using a standard base across all sites the system 20 indicates where a particular facility is in relation to others and to help make general predictions. However, over time the system 20 knows exactly what happens at a facility at key GDD indicator levels.

The Soil Degree Day-GDD Indexes is preferably monitored using soil temperature, moisture and salinity sensors 33 at ambient temperature. Weighted average formulas are used for these indexes. This is similar to the Degree Day model above but with the traditional Growing Degree Day model to compare soil degree days with ambient growing degree days for reference.

Figure 18:
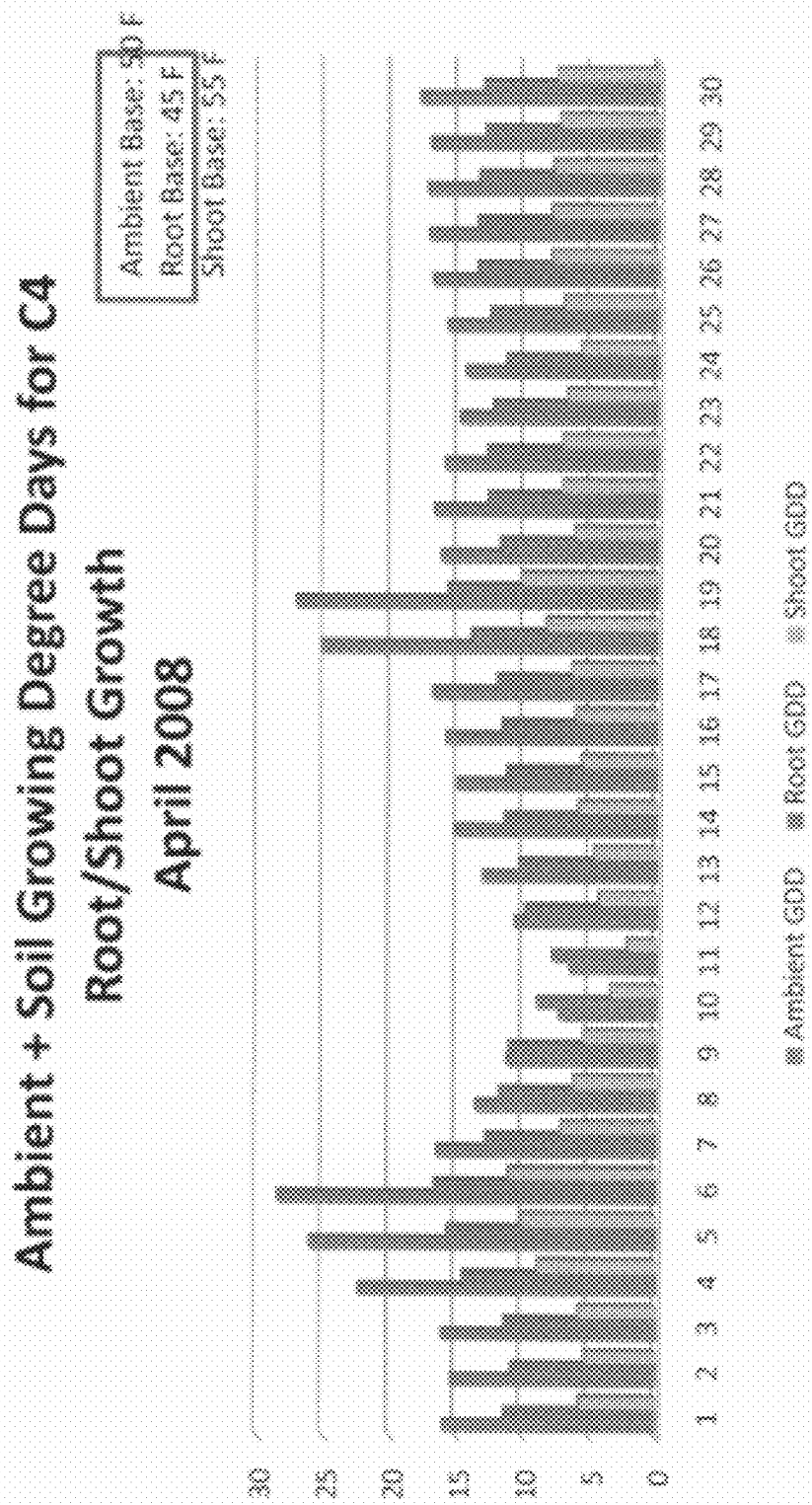
FIG. 18 is a graph of ambient plus soil growing degree days for C4 root and shoot development.

FIG. 18 illustrates ambient and soil GDD values for C4 root/shoot growth for April. While the ambient base is the same, the root and shoot bases are different to accommodate the warmer temperatures necessary for stimulating early root and shoot growth.

Figure 19:
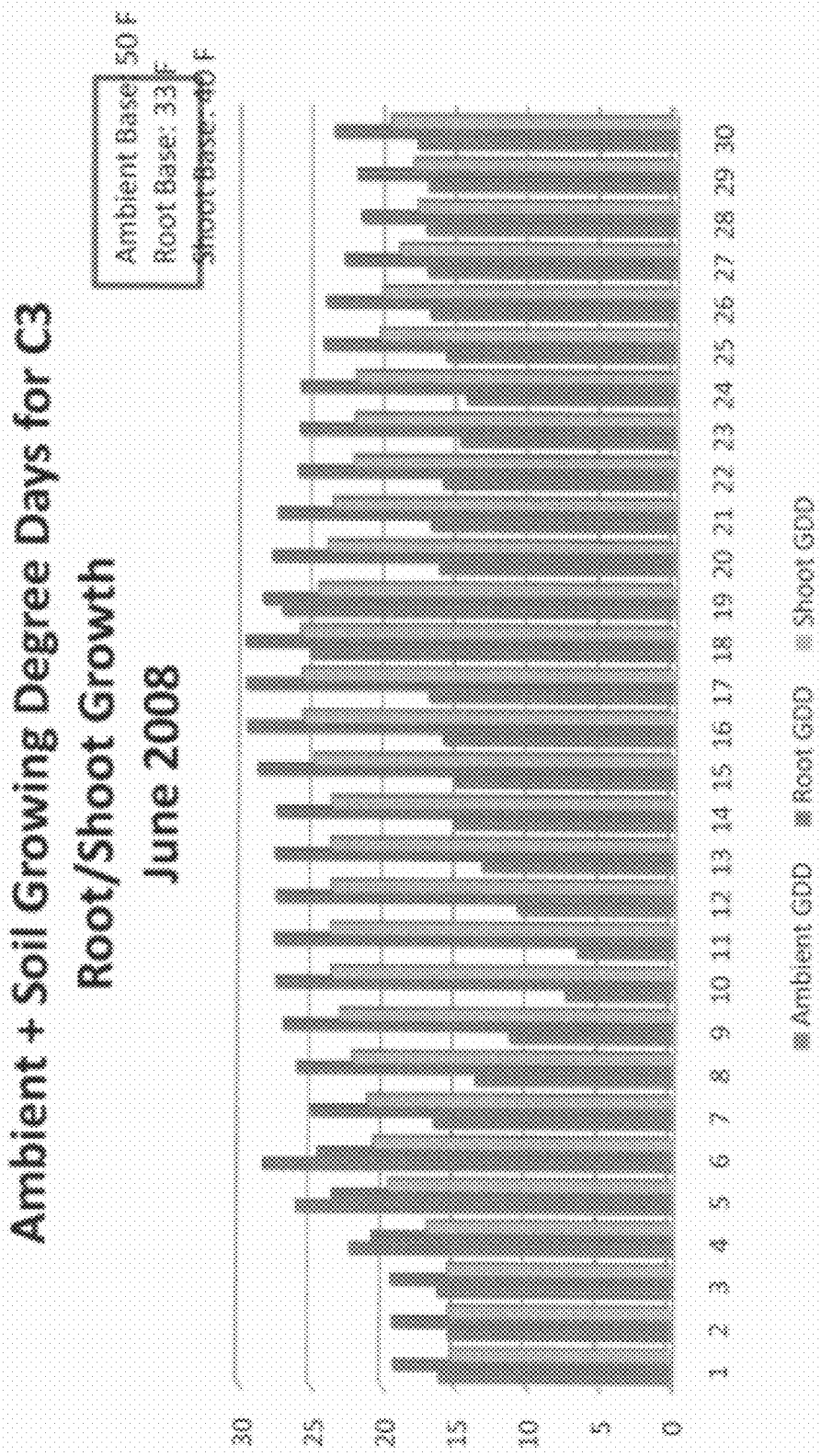
FIG. 19 is a graph of ambient plus soil growing degree days for C3 root and shoot development.

FIG. 19 illustrates ambient and soil GDD values for C3 root/shoot growth for June. This is the same as FIG. 17 except in June.

Figure 20:
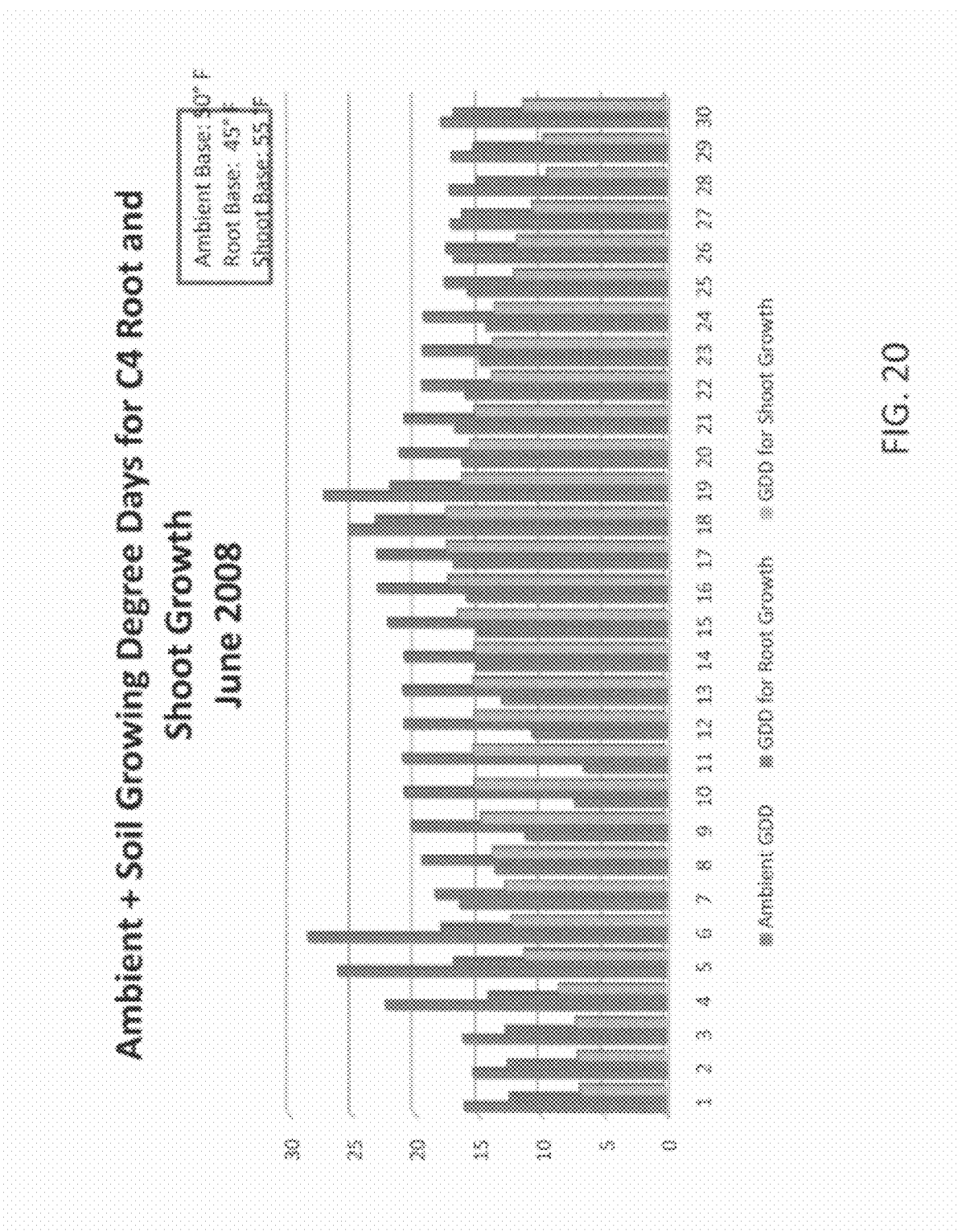
FIG. 20 is a graph of ambient plus soil growing degree days for C4 root and shoot development.

FIG. 20 illustrates ambient and soil GDD values for C4 root/shoot growth for June. This is the same as FIG. 18 except in June.

Figure 21:
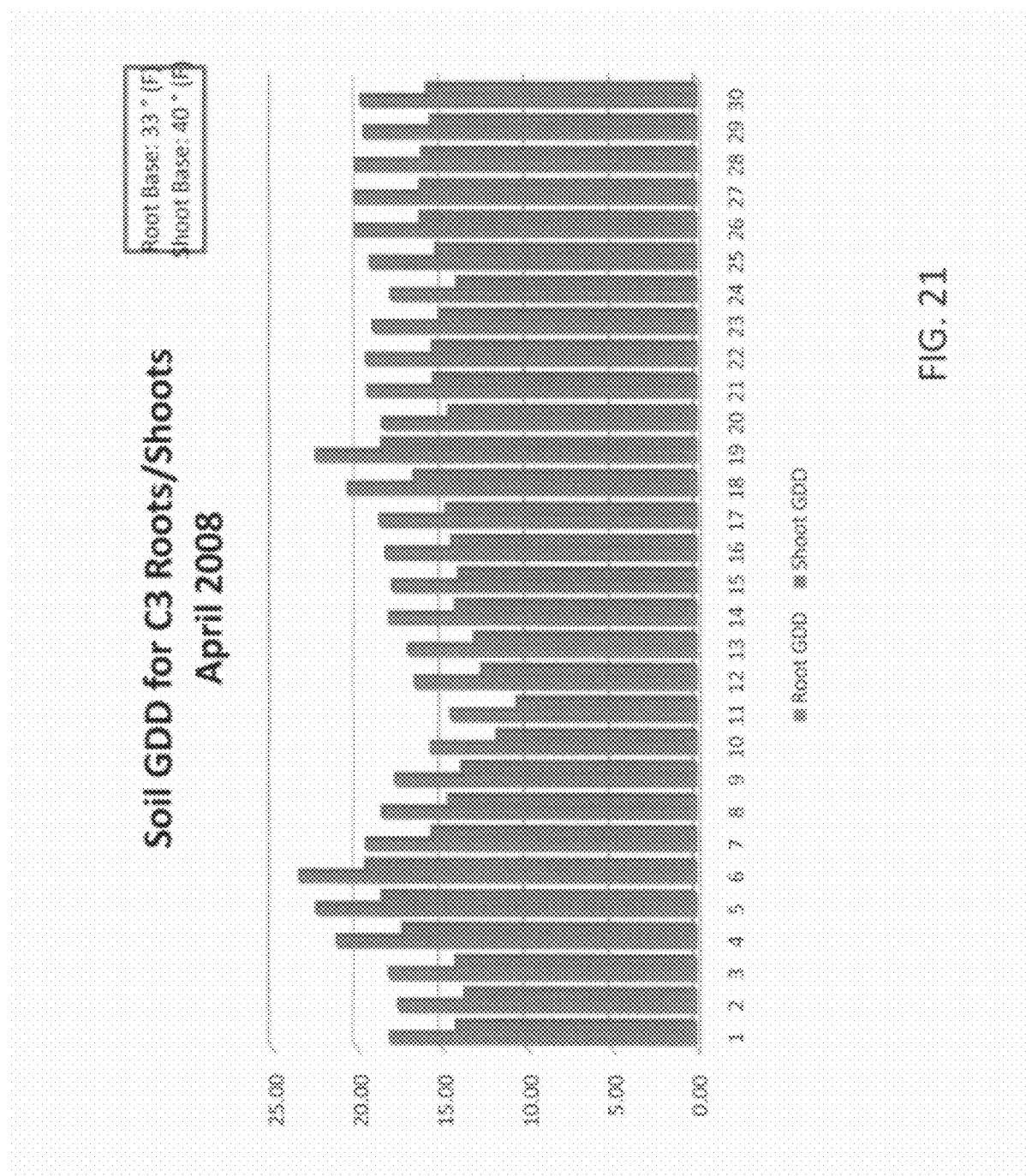
FIG. 21 is a graph of soil GDD for C3 roots and shoots.

FIG. 21 illustrates soil growing degree days for C3 roots/shoots for April. This chart illustrates soil only data calculations of growing degree days. While this chart shows the daily values over the course of a month, it makes it easy to compare one day to the next. GDD information accumulated over time by the system provides tremendous information to an operator. This chart indicates a prime time to adjust fertilizer nutrition to feed roots versus shoots.

The Temp-Moisture-Salinity Index is preferably monitored using soil temperature, moisture and salinity sensors. A weighted average formula is used for this index. Outputs are the results of a combined weighted average formula that considers the ideal temperate, moisture and salinity for a site specific plant and soil type. By assigning a value to each variable and then determining that value by measuring where the variable is in relation to what is optimum for that site's plant and soil, the system 20 combines the results from each of the three key soil variables (temp, moisture, salinity) to determine an overall condition of the site so that adjustments are made to correct the issue, cultural practices are employed in a more timely and effective manner, and plant health and performance are maximized.

In other words, if a facility is making fertilizer applications based on calendar date, and this application is heavy in nitrogen at a time that is not conducive for shoot growth, the facility compromises the overall effectiveness of that application even if it is a "slow release" form of nitrogen. This includes forcing top growth at the expense of root growth, leaching of excessive nitrogen and not gaining maximum output from the application. In turf, for instance, when root mass is fed, a return on investment comes by way of tissue growth from the crown up. But if one feeds shoot mass one sees the opposite in root growth. Charts provided by the system 20 help the user dial in fertilizer applications particularly in the early and late parts of the season.

Figure 22:
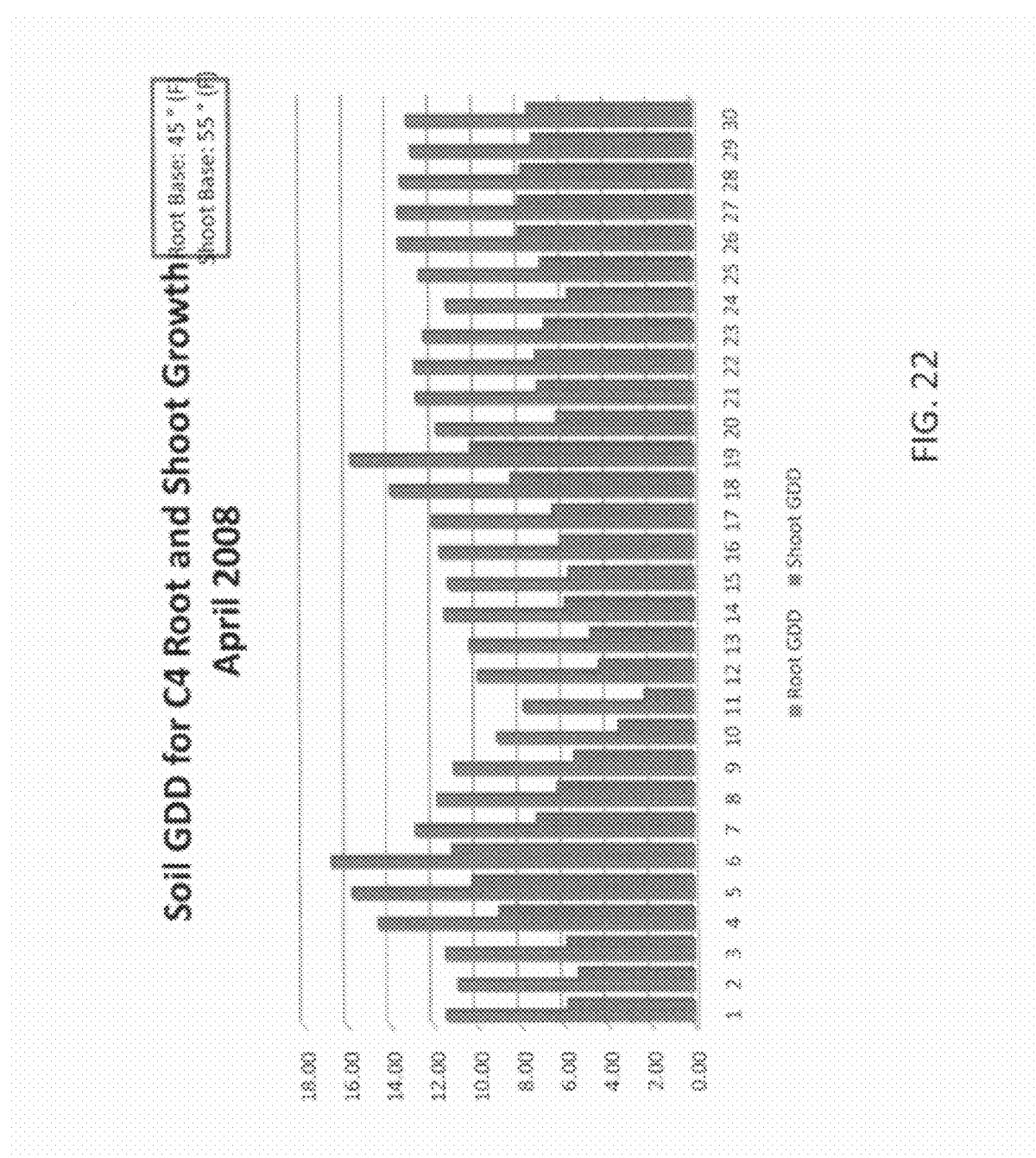
FIG. 22 is a graph of soil GDD for C4 root and shoot growth.

FIG. 22 illustrates soil growing degree days for C4 roots/shoots for April. This is the same as in FIG. 21 except for C4 turfgrass.

Figure 23:
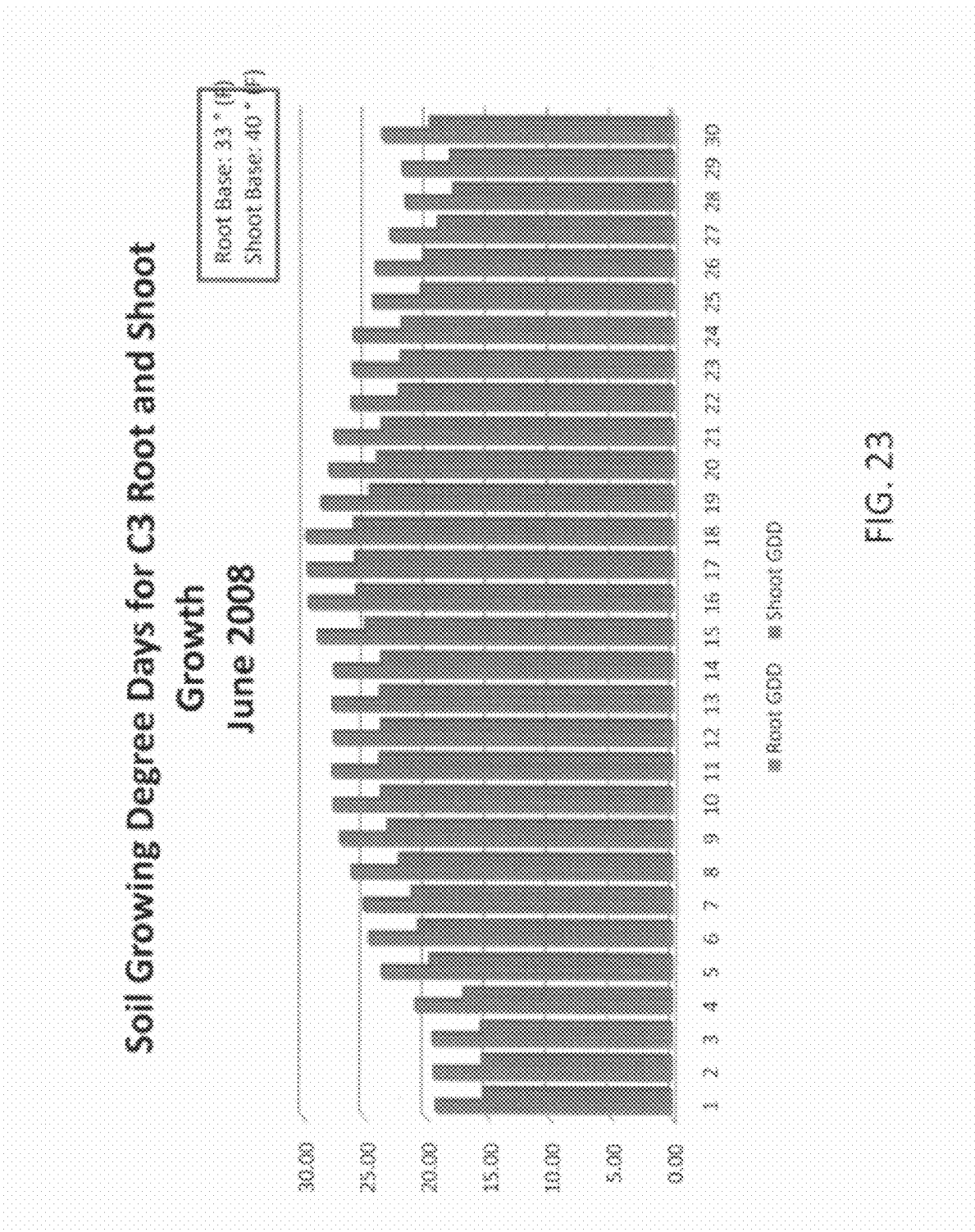
FIG. 23 is a graph of soil GDD for C3 root and shoot growth.

FIG. 23 illustrates soil growing degree days for C3 roots/shoots for June. This is the same as FIG. 21 but for C3 turf in June to show comparison. Notice the much higher degree days for each day than those for April. It is likely that breaking points are seen in specific activities at specific sites when 27 GDD are accumulated for a day in June.

Figure 24:
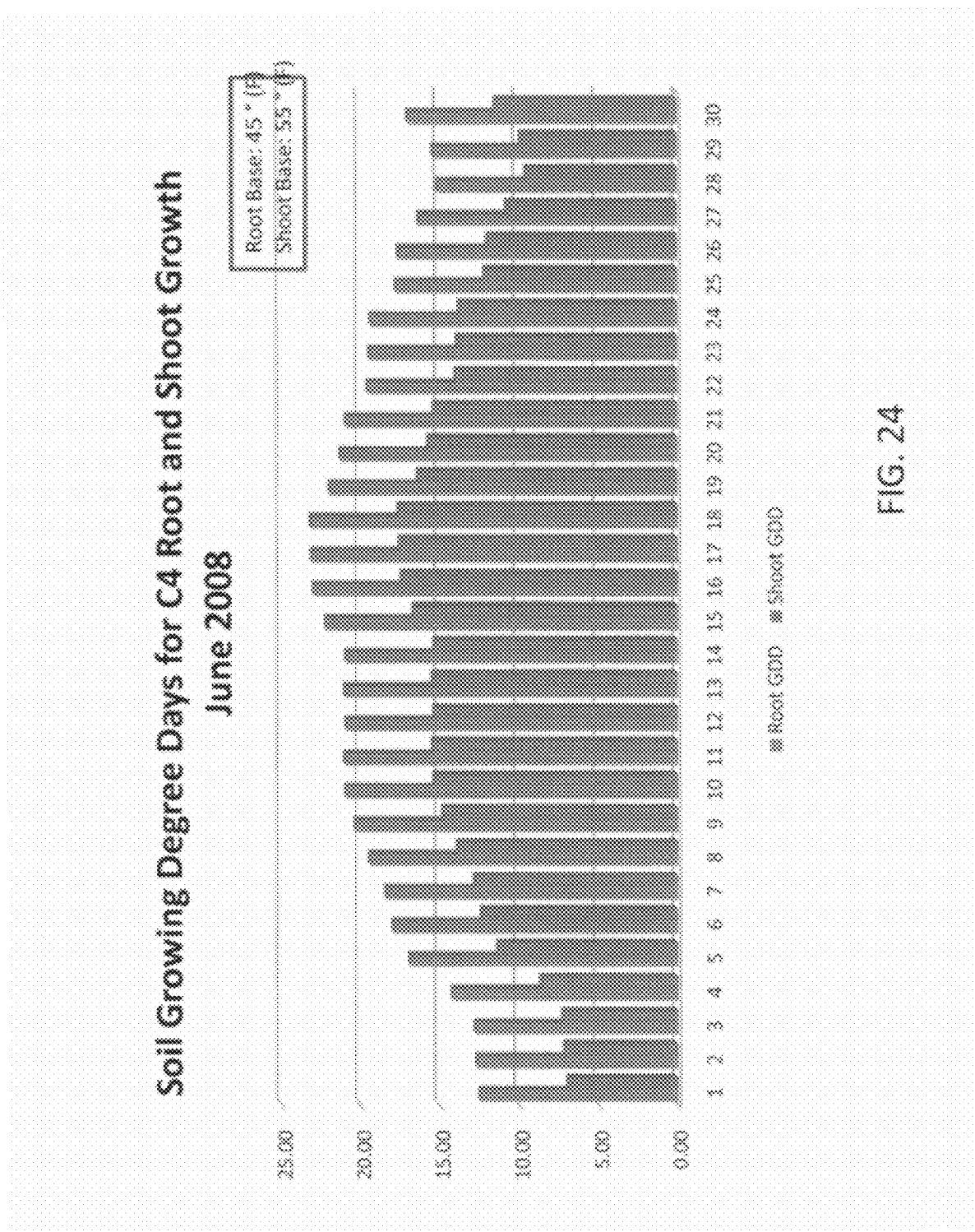
FIG. 24 is a graph of soil GDD for C4 root and shoot growth.

FIG. 24 illustrates soil growing degree days for C4 roots/shoots for June. This is the same as FIG. 22.

Figure 25:
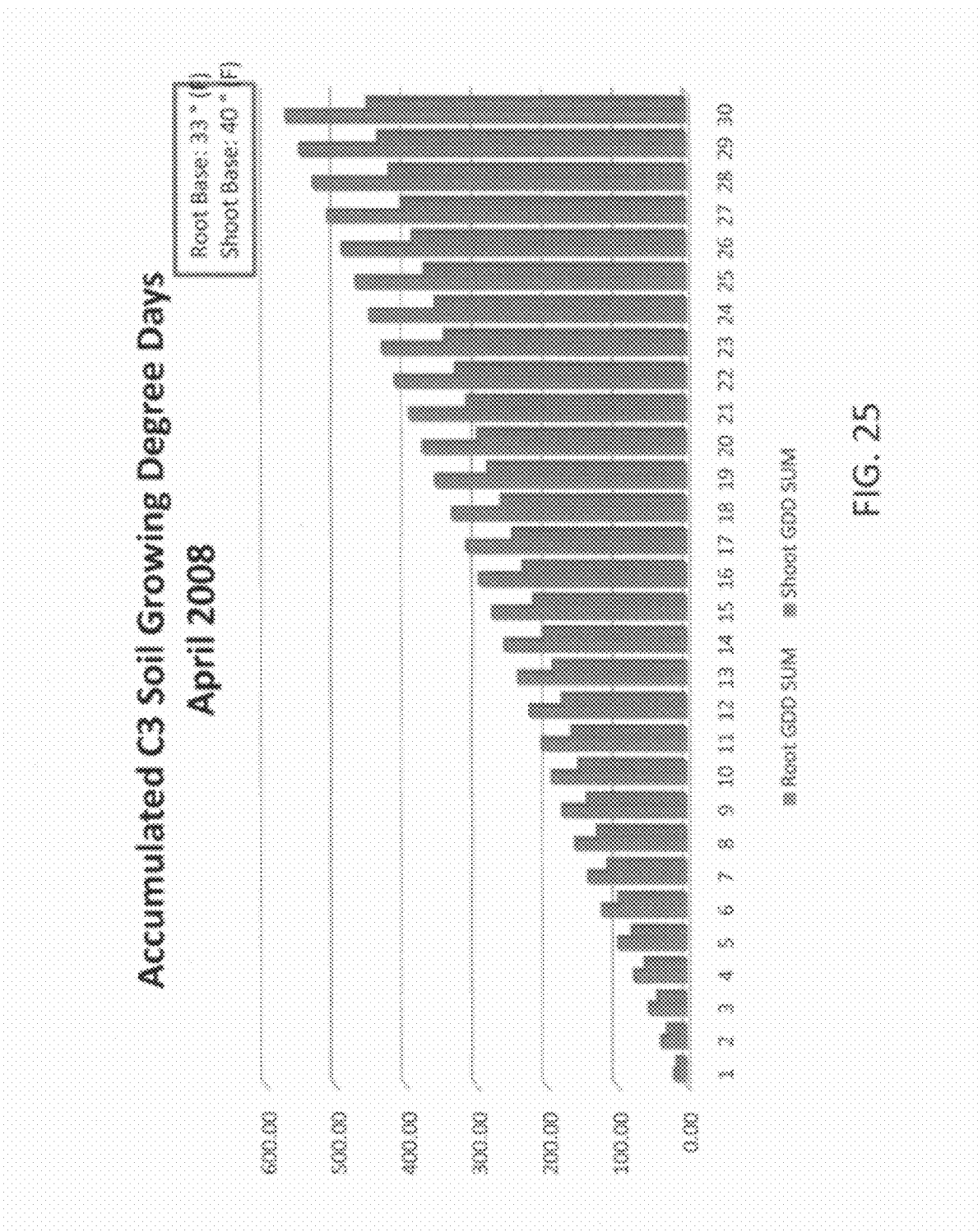
FIG. 25 is a graph of accumulated C3 soil GDD.

FIG. 25 illustrates accumulated C3 soil growing degree days for April. This chart shows the accumulated SOIL Growing Degree Days for the month of April using sample data. This particular chart does not take into account the upper limit for root growth. In other words, there is a threshold where roots start declining due to soil temperatures and thus GDD are reduced.

However, having accumulated GDD is very useful to tag the timing of particular events at specific sites. For instance, at 97 GDD for root development on Green 3, the first outbreak of Bermuda grass decline (GGA) was seen, or at 48 GDD on Green 7, 90% of the *Poa annua* seed heads emerge were seen. The "tags" are infinite and require user input. But over time this grows on itself and becomes more and more powerful as a tool.

If Bermuda grass decline is analyzed, the same pathogen, *Gaeumannomyces graminis*. Var. *avenae* (GGA) that causes this disease in Bermuda grass also causes Take All Patch in bentgrasses and ryegrasses as well as bluegrasses of C3 turf. Research has documented that this pathogen thrives at soil temperatures of 70° F. When it reaches its climax, turf declines and it can be rapid particularly in Bermuda grass.

Using the GDD model of the system 20 set up for this pathogen, the system 20 finds the optimal time for control measures. One very environmentally sound practice is to utilize Manganese (Mn) in the soil. Since GGA is a soil born pathogen, it has devised some biological methods of its own that greatly affect turfgrass growth. One in particular is the ability of the pathogen to oxidize Manganese in the soil to make it unavailable for plant uptake. This proves to be a very important process as this lack of Manganese has an effect on several physiological processes in the plant . . . the most important of which is photosynthesis (Ps) since Mn is called on for the initial stage of Ps. As Ps is diminished the plant loses its ability to make necessary sugars and compounds that can fight off the pathogen or that are used to grow through any induced stress. The decline can be swift and lethal in many cases. Using a soil based GDD model set up for this pathogen (or any stress) helps time soil applications of Manganese or employ other practices to offset the imminent decline associated with that growth stage. Again, this is another novel tool of the system 20 to use for making sound management decisions by an operator of the land area.

Figure 26:
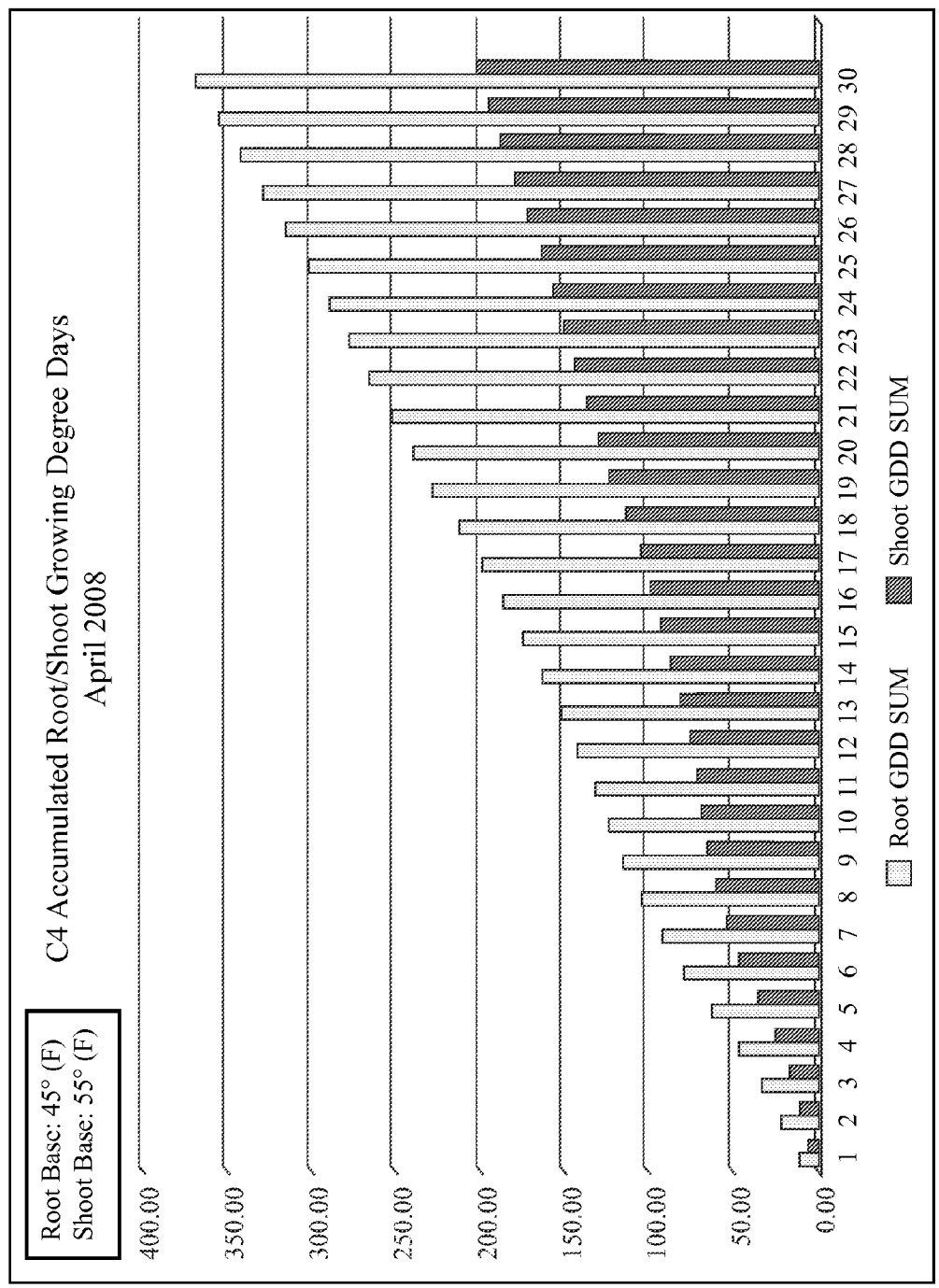
FIG. 26 is a graph of accumulated root and shoot GDD.

FIG. 26 illustrates accumulated C4 soil growing degree days for root/shoot growth for April. This is the same as FIG. 25 except it includes turf appropriate base levels.

Figure 27:
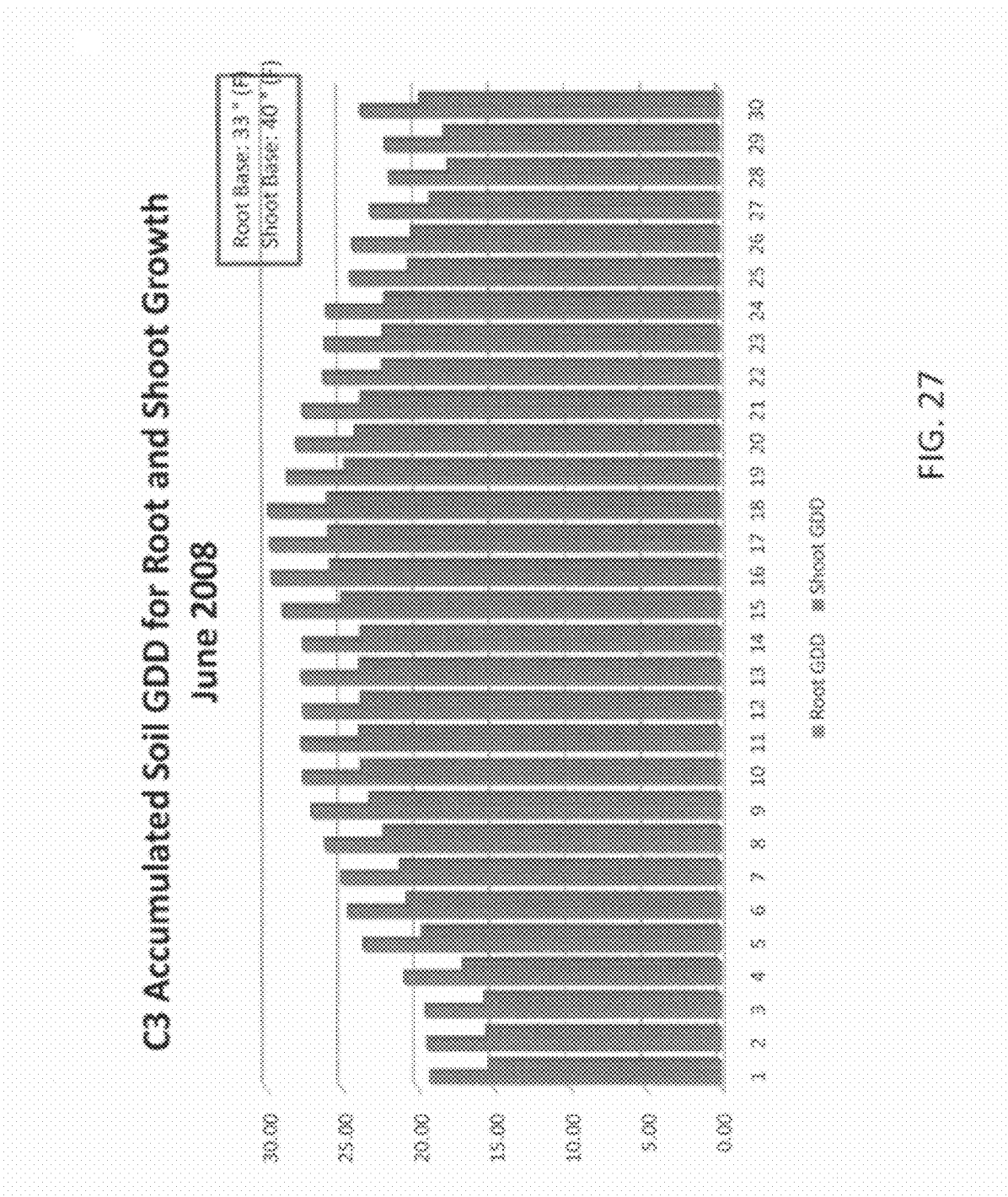
FIG. 27 is a graph of C3 accumulated GDD for root and shoot growth.

FIG. 27 illustrates accumulated C3 soil growing degree days for root/shoot growth for June. This is the same as FIG. 25 except it includes June data for comparison.

Figure 28:
FIG. 28 is a graph of C4 accumulated GDD for root and shoot growth.

FIG. 28 illustrates accumulated C4 soil growing degree days for root/shoot growth for June. This is the same as FIG. 26 except for C4 Turf in June to show a comparison.

Figure 29:
FIG. 29 is a graph of soil pathogen and stress GDD (daily and accumulated.

FIG. 29 illustrates soil pathogen/stress GDD (Daily, Accumulated). This GDD model is based solely on soil data and is set up for a particular stress. In this case a base is set at 65° F. which is a base temperature for many pathogenic fungi to exist in an active state. The more days at or above this base, the more days development of that pathogen population or stress load. One can set this base at any level one wants for particular target "pests" or stresses. This is similar to the root/shoot GDD models but it can be designed for a specific target instead of a simple accumulation based off of root/shoot stimulation which is basically the same as a general growth model. Instead of measuring the general growth of the plant, the system 20 is preferably measuring the growth of a particular stress or pest.

Figure 30:
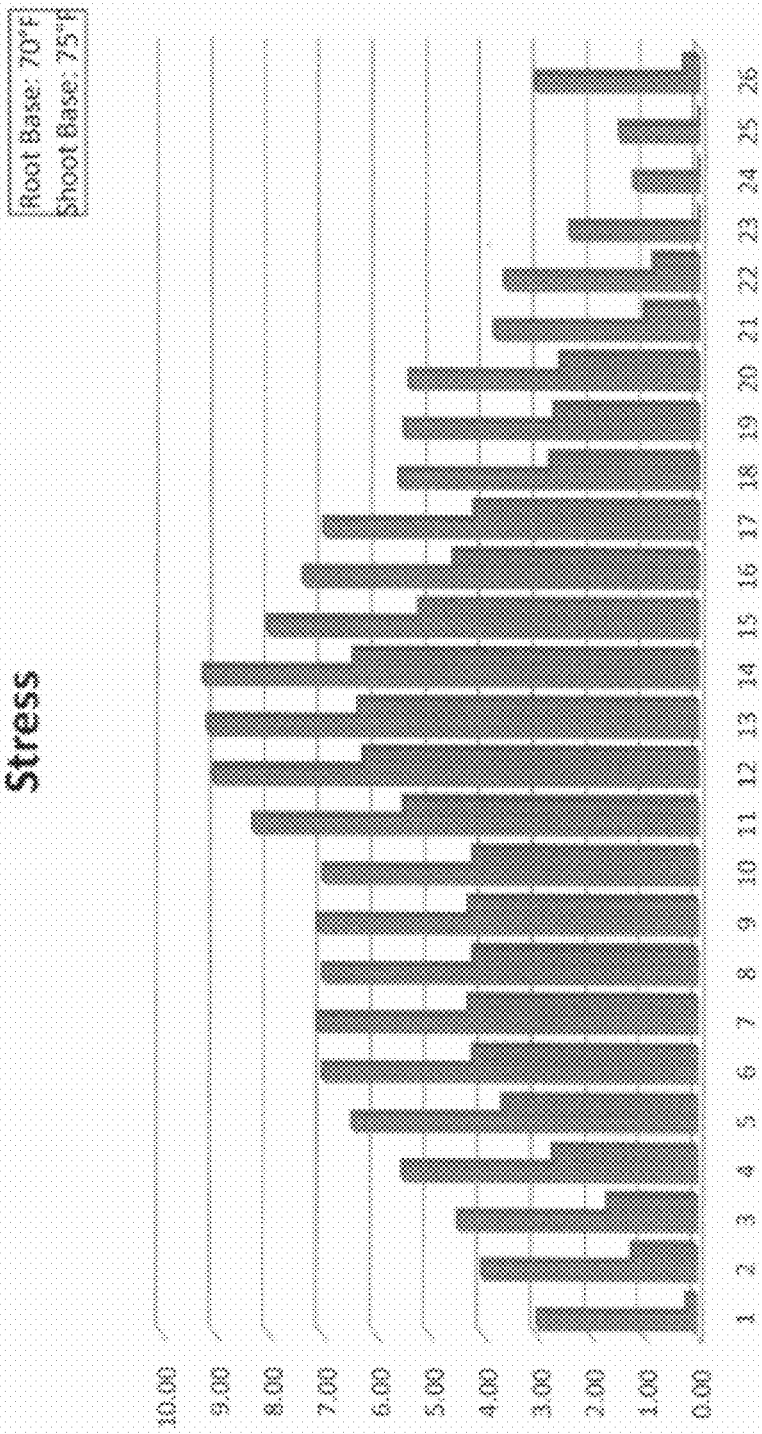
FIG. 30 is a graph of soil daily degrees days for root and shoot decline from heat stress.

FIG. 30 illustrates soil degree days for root/shoot decline from heat stress. Temperature is the single most important factor in the soil for initiating or eliminating certain plant responses. It has been heavily documented over the years that temperature triggers for root and shoot stimulation are very accurate and predictable. The system 20 monitors these conditions in real time. This graph shows the daily degree days for root/shoot decline based on certain conditions. In this case, it is calculating root and shoot decline by showing how many degree days past this base are during hot conditions. The base used for root decline is 70° F. and shoot decline is 75° F.

It is likely that a course that has been managed under severe stress for years will have a higher tolerance level (higher base threshold) than one that has not been managed under stress. However, having a base of comparison is important. This chart shows the daily degree days over the threshold. A DD of 7 or greater shows great stress on root growth and could warrant the use of certain biostimulants and micronutrients to help manage through the stress. At the same time, a nitrogen application on a day that is showing stress at this level could mean great root loss if not managed correctly.

Research in the field for golf and sports turf facilities shows the loss of more than 70% root mass in less than 24 hours. So this novel indicator of the system 20 is another good stress indicator tool.

Figure 31:
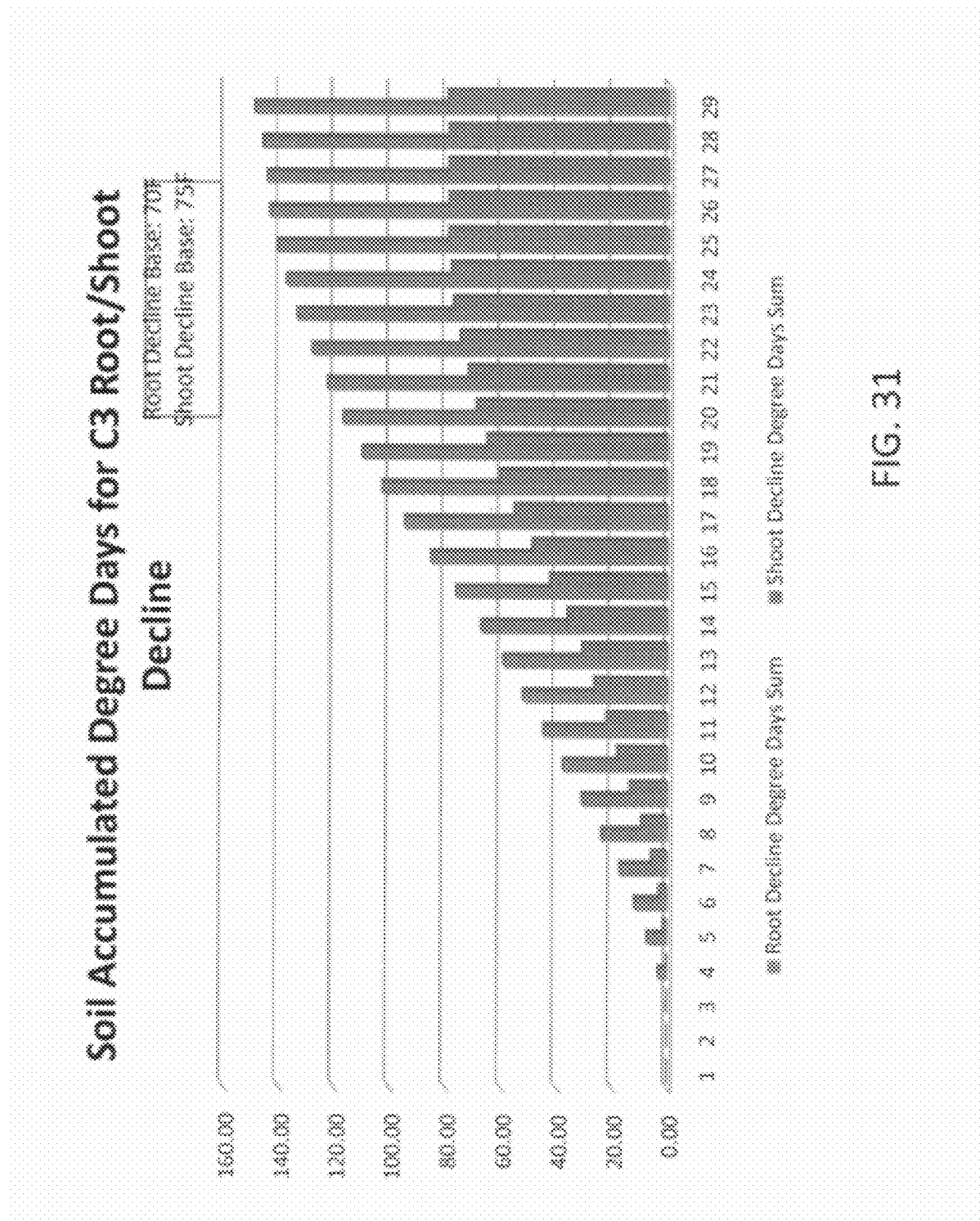
FIG. 31 is a graph of soil accumulated degrees days for C3 root and shoot decline.

FIG. 31 illustrates soil accumulated degree days for C3 root/shoot decline.

This chart shows the same as FIG. 30 but it is accumulating the degree days rather than just showing the daily degree days. There may be certain episodes that occur at certain accumulated degree days which only time will show at each site.

Figure 32:
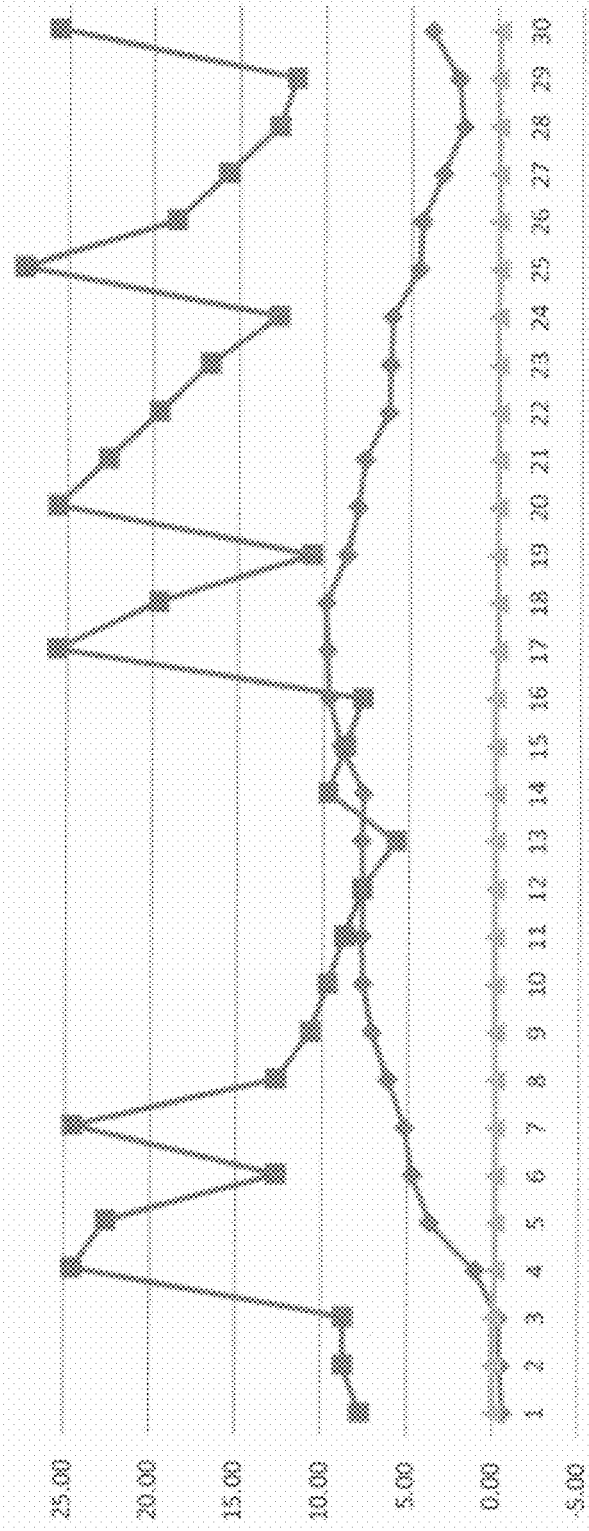
FIG. 32 is a graph of the variance of soil temperature, moisture and salinity from optimal levels.

FIG. 32 illustrates variance of soil temperature, moisture and salinity from optimal conditions. What are optimal conditions? Fundamental scientific research and data provides some indication but the system 20 is more powerful, especially after one season of data collection. There is a point when everything in a turf system goes correctly and a sound turfgrass manager knows exactly when that is. By having user input, the present invention can correlate the conditions of the soil at the time when things are ideal. The system 20 can log that data and adjust the optimal conditions levels. Then with a tool like this graph the system 20 shows a user where they are in relation to that optimal level at any time.

Optimal soil moisture is initially dialed in based off of soil analysis that tells what the soil's porosity is, the OM %, the Field Capacity (FC) and texture. From the porosity and FC, the system 20 determined what the optimal moisture percentage is for growth. Research and experience tells that for nearly all plants the optimal moisture percentage is approximately 75% of Field Capacity. So if a soil's Field Capacity is 28% then its optimal moisture for plant growth would be 21% (0.75*28). The system 20 then measures how far it is from this level at any time with wireless technology of the system 20. This optimal level may not apply to golf course greens as it stands today, one realizes this from experience knowing that most putting green (and other golf course areas) species of turf can perform very well at levels below this "optimum" level. The index always tells where the system 20 is in relation to this optimal level as the optimal level is adjustable for every site.

The temperature level is based off of models developed through research for root and shoot growth. For instance, one knows that roots cease to produce root hairs in C3 turf at 77° F. but this decline actually begins at 70° F. on average (85° F. in C4 Turf). There are also thresholds set for shoot growth. Sites can vary based off of varietal and genetic differences or simply based off of conditioning practices over the years that have altered the plants phenological activities. A fine example of these phenological variances is when the system 20 considers the multitude of *Poa annua* appearances throughout the world. The system 20 takes *Poa* plants with very similar genetic make ups, manages them completely different and sees very different plants as far as their performance goes. But one thing that does shine through is that every plant does have a threshold for root and shoot growth as it relates to temperature, which is monitored by the system 20 and adjusted over time.

For EC variation, this is a little more complex. EC levels can be affected by water, environmental occurrences, cultural practices, particularly fertilizer inputs, and simply from plant activity. Plants literally produce salts that mingle with microorganisms who feel off of those compounds then bring something back to the plant. This is called microbial facilitation by the way and it occurs constantly. It gets exponentially greater as the soil moisture and temperature levels rise (to a certain point where the activity declines).

One thing the system 20 does with EC is that when irrigation water conditions are known, particularly if a sensor is put directly in a wet well, and the system 20 knows the soil chemical makeup (from the soil test), then if the system 20 sees fluctuations in soil EC with the water conditions remaining fairly consistent, then the system 20 predicts salt movement from plant and biological activity in the soil based off of real time monitoring. Logging nutritional inputs and taking a look at this activity also helps optimize those fertilizer applications more effectively over time.

Through a growing season and monitoring a plant when these occurrences take place, then the system 20 makes predictions and adjusts cultural practices to manage them more effectively. For instance, if the system 20 sees spikes in EC at certain temperature and moisture levels and the team of laborers report that they took twice as many clippings off of the greens during the period, then the system 20 provides a correlation between EC activity and top growth. That is just one example of user input capability in the system 20.

Figure 33:
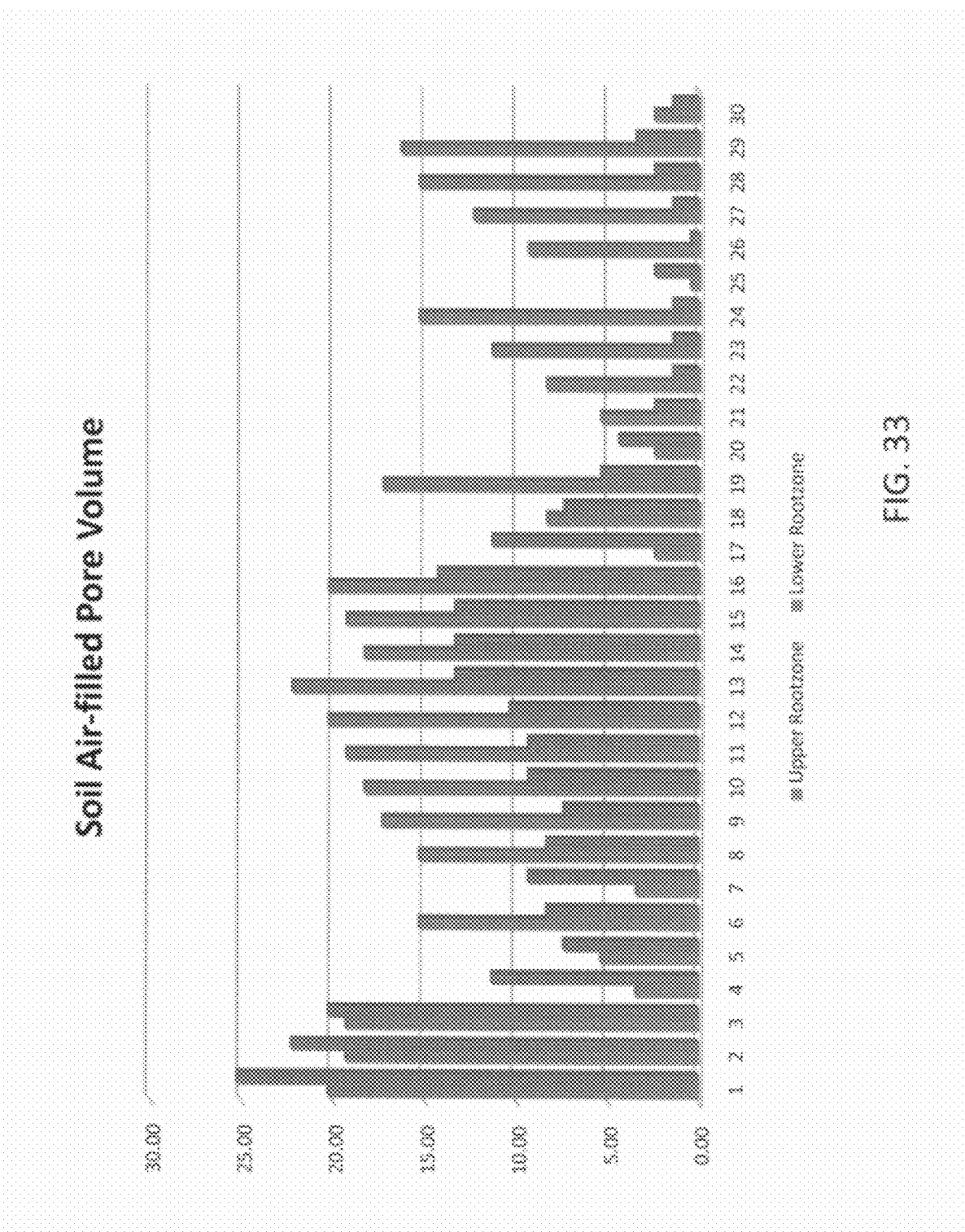
FIG. 33 is a graph of soil air-filled pore volume.

FIG. 33 illustrates soil air-filled pore volume. While the system 20 does not directly measure air in the soil, the system 20 does measure moisture, or water-filled pore space. In a soil there are solids and spaces between those solids. Some argue that organic matter is not technically a solid but in reality it is because it is not a space, it is something that occupies space. Knowing the total porosity of a soil (obtained from the porosity soil test, or estimated from soil texture and bulk density) and knowing what volume water is occupying, then the system 20 subtracts the difference between total pore space and water-filled pore space to get air-filled pore space.

In soil if water is not occupying the pore spaces then a gas is. However, this gas is not necessarily oxygen (diffused $O_2$). It may likely be $CO_2$ which often gets trapped in the soil. Either way, low air space is not healthy for the plant in any respect. The most important aspect of this is due to the influence of anaerobic respiration where the plant will actually produce ethanol in the soil. This gas is toxic to the plants and has a great impact on root development and necessary growth. Research shows that if any part of the root system is in contact with an anaerobic (no oxygen) part of the soil, then anaerobic respiration takes place and many other detrimental activities occur. This influential airless region can be as minimal as 2 mm thick to cause problems.

With golf courses, particularly putting greens, anaerobic respiration is the number one reason for deterioration of root mass. Many times layers form and trap water, particularly if the layer is an organic matter rich layer. In addition, the underlying gases that come out of roots, primarily $CO_2$ ($O_2$ goes in) cannot escape the soil nor can oxygen get to the bottom of the root mass. Research supports that $CO_2$ primarily comes from the soil for photosynthesis in the leaves, much more so than from the air environment above the soil. So this lack of escaping gas has a huge impact on plant health and performance.

With charts that show the air space based off of the measured water content while knowing the porosity of the soil, calculated in real time, reviewing a bar graph allows one to make decisions of deep tine aerification or spiking or one of many other possible practices designed to force air into the soil and allow gas to escape. One can also predict layers in the soil. For instance, high air content in the upper profile and significantly low air content in the lower rootzone probably means that the air is having trouble making it into the profile. It will be important however to realize that some soils simply hold a lot of water in the deep profile. If that water has nowhere to go then it can wick up continuously and management practices must take this into account. However, every soil should be able to produce acceptable moisture and air contents to at least 6 inches in depth. Sensors of the system 20 are typically above this region on golf courses and sports facilities.

The Salt Load Index is monitored using soil temperature, moisture, and salinity sensors 33. A weighted average formula is used for this index. This index requires a lab analysis of the soil and the irrigation source so that the total salt breakdown is known to identify the key salts in that system. By knowing what the total salt analysis is in both the soil and the water, and by measuring in real time the salinity variance in the soil, the system 20 determines the total salt load on the plant in terms of a mass per given area (ex. lbs of salt per acre). The system 20 determines the effects of drying down that soil and the potential soil structure deterioration as salts can break apart soil structure when it hydrates, precipitates and then rehydrates in the soil environment. This process causes some salts to get very large when wet and then very small and very large again as they dry and re-wet. This is a serious problem in soil management since it can clog pores spaces, affect water, nutrient and root movement through the soil and greatly impact plant health.

The Putting Speed Index is monitored using soil temperature, moisture, and salinity sensors 33, preferably at ambient temperature. A weighted average formula is used for this index. The system 20 knows that with all things being equal such as mowing patterns, mowing quality and height of cut, and consistent management practices that the soil conditions greatly affect the putting speed on golf course greens. This also applies to fairway roll on golf course fairways. Monitoring the real time soil conditions, and getting inputs from the user who monitors his putting speed, the system 20 can easily match the conditions with the speed at any given time. For tournament play or other time when the user wants to increase putting speed, traditionally he would lower his height of cut and do other cultural practices to gain that speed. While these practices can still be employed, the dependency on them can be reduced by managing the soil beneath the surface. For instance, experience has shown that only a 2% change in soil moisture with no change in cutting height or cultural practice can have a 6 to 8 inches increased roll on a typical putting green. This is well desired performance in putting green conditioning. Using this model on fairways, a 2% reduction in soil moisture can result in several feet of roll with all other conditions the same. Furthermore, a 2% reduction in water over several acres easily equates to a potential water savings in the thousands and tens of thousands of gallons.

The Air Exchange Index is preferably monitored using a soil moisture sensor 33. The formula is: Total pore %−Moisture %=Air Exchange %. Air Exchange % is the present pore space that is allowing for air exchange, a very key indicator of plant health that is easily measured in real time by technology of the system 20. By knowing how much water is in a soil, the system 20 subtracts this from the total pore space (identified in soil analysis). For example if the total pore space is identified as 45% and 28% moisture is measured, then the air exchange % is 45-28=17%. This allows the user to watch closely how the upper and lower rootzone qualities may change. This will easily indicate a developing problem such as a layer that is holding water and therefore reducing air exchange. The lack of air exchange is very detrimental to the plant by limiting physiological activities, respiration and growth.

The Optimum Moisture % is preferably monitored using soil moisture sensors 33. A weighted average with soil analysis is used for this, which informs the user what the optimum moisture is for his specific soil and where he is in relation to that level at all times through real time representative wireless monitoring. Every soil has a specific percentage of solids and pore spaces. These are identified through lab analysis. Ideally when considering water and air availability to the plant, half of the pore spaces are filled with water and half with air. This typically does not exist due to physical qualities of the soil which is explained below. When it comes to performance in turfgrass or any plant, there is an optimum level where adequate water and air exist while the plant achieves maximum performance, health and/or yield. The system 20 monitors how much of the total volume of soil is filled with water, and therefore also measures how much is filled with air. Typically the solids (sand, silt, clay, organics) fill up about half of the soil with the other half pore space. For example, if a lab shows a soil to have 46% pore space (54% solids), of that 46% there is an optimal level where water is available. To know this, the system 20 identifies the soil's field capacity (lab analysis) which is the point where the soil can no longer hold any addition water without losing it to gravity. Research has shown that 70-75% of FC is the point where the most available water exists for plant uptake. In this example, FC was identified as 29%. The optimum available water % would be 0.70×29%=20%. If the user manages his soil to maintain this 20% target he will optimize moisture availability to the plant. He may dry down the level from here to further dial in precision based on field expectation, desires and performance tolerances. The system 20 allows this user to know exactly where he is in relation to where he should be at any time in real time.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention:

1. A system for monitoring real-time conditions of a land area, the system comprising:

a plurality of first sensor nodes and a plurality of second sensor nodes, each of the plurality of first sensor nodes positioned approximately 2 inches to approximately 2.5 inches below a surface of the soil area in proximity to an active root system mass and in an upper soil area, each of the plurality of second sensor nodes positioned approximately 3 inches to approximately 5 inches below a surface of the soil area in proximity to a bottom of a root mass and in a lower soil area, wherein the lower soil area is below the upper soil area, each of the plurality of first sensor nodes comprising a housing, a processor, a wireless transceiver, a salinity sensor, a moisture sensors, a temperature sensor, and a power supply, each of the plurality of second sensor nodes comprising a housing, a processor, a wireless transceiver, a salinity sensor, a moisture sensor, a temperature sensor, and a power supply, each of the first plurality of sensor nodes configured to monitor and wirelessly transmit through the soil a real-time upper soil moisture value, a real-time upper soil temperature value and a real-time upper soil salinity value, each of the second plurality of sensor nodes configured to monitor and wirelessly transmit through the soil a real-time lower soil moisture value, a real-time lower soil temperature value and a real-time lower soil salinity value;

a wireless transceiver in communication with a processor, the wireless transceiver configured to receive the real-time upper soil moisture value, the real-time upper soil temperature value and the real-time upper soil salinity value from each of the first plurality of sensor nodes and to receive the real-time lower soil moisture value, the real-time lower soil temperature value and the real-time lower soil salinity value from each of the second plurality of sensor nodes, the processor configured to generate a real-time upper soil and lower soil moisture variance; and means for communicating the at least one parameter to an operator of the land area, the communicating means communicating the real-time upper soil and lower soil moisture variance to a user of the land area.

2. The system according to claim 1 wherein the processor is also configured to determine a fairway speed index value, a putting speed index value, or a salt load index value.

3. The system according to claim 1 wherein the processor is also configured to generate a real-time evapotranspiration value for plants in the soil area.

4. The system according to claim 1 wherein the processor is configured to determine a growth decline point for a plant in the soil area.

5. The system according to claim 1 wherein the processor is configured to calculate at least one of a plurality of parameters for soil degree day values comprising root stimulation, leaf stimulation, disease pathogens, insect development, heat stress load, dormancy triggering, site specific stresses.

* * * * *